US010787687B2

(12) United States Patent
Vainio et al.

(10) Patent No.: US 10,787,687 B2
(45) Date of Patent: Sep. 29, 2020

(54) METHOD OF PROCESSING LIGNOCELLULOSIC MATERIAL USING A CATIONIC COMPOUND

(71) Applicant: NESTE OYJ, Espoo (FI)

(72) Inventors: Heidi Vainio, Espoo (FI); Olavi Myllymaki, Espoo (FI); Ville Pihlajaniemi, Helsinki (FI); Mika Sipponen, Espoo (FI); Simo Laakso, Turko (FI); Ilkka Lehtomaki, Helsinki (FI); Ossi Pastinen, Kantvik (FI); Perttu Koskinen, Helsinki (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/103,707

(22) PCT Filed: Dec. 11, 2014

(86) PCT No.: PCT/EP2014/077465
§ 371 (c)(1),
(2) Date: Jun. 10, 2016

(87) PCT Pub. No.: WO2015/086783
PCT Pub. Date: Jun. 18, 2015

(65) Prior Publication Data
US 2016/0319310 A1    Nov. 3, 2016

(30) Foreign Application Priority Data

Dec. 11, 2013    (EP) ..................................... 13196742

(51) Int. Cl.
| C12P 7/64 | (2006.01) |
| C12P 19/02 | (2006.01) |
| C12P 19/14 | (2006.01) |
| C08H 8/00 | (2010.01) |
| C08B 37/00 | (2006.01) |
| C08H 7/00 | (2011.01) |

(52) U.S. Cl.
CPC ............ *C12P 7/64* (2013.01); *C08B 37/0057* (2013.01); *C08H 6/00* (2013.01); *C08H 8/00* (2013.01); *C12P 19/02* (2013.01); *C12P 19/14* (2013.01); *C12P 2201/00* (2013.01); *C12P 2203/00* (2013.01)

(58) Field of Classification Search
CPC .. C12P 19/02; C12P 19/14; C12P 7/64; C12P 2203/00; C12P 2201/00; C08B 37/0057; C08B 8/00; C08B 6/00
See application file for complete search history.

(56) References Cited

U.S. PATENT DOCUMENTS

| 7,691,792 | B1 | 4/2010 | Fisher et al. |
| 2008/0032344 | A1 | 2/2008 | Fallavollita |
| 2009/0004715 | A1 | 1/2009 | Trimbur et al. |
| 2009/0011480 | A1 | 1/2009 | Trimbur et al. |
| 2009/0035842 | A1 | 2/2009 | Trimbur et al. |
| 2009/0047721 | A1 | 2/2009 | Trimbur et al. |
| 2009/0061493 | A1 | 3/2009 | Trimbur et al. |
| 2009/0148918 | A1 | 6/2009 | Trimbur et al. |
| 2010/0323413 | A1 | 12/2010 | Trimbur et al. |
| 2010/0323414 | A1 | 12/2010 | Trimbur et al. |
| 2011/0014665 | A1 | 1/2011 | Trimbur et al. |
| 2011/0015417 | A1 | 1/2011 | Trimbur et al. |
| 2011/0047863 | A1 | 3/2011 | Trimbur et al. |
| 2011/0190522 | A1 | 8/2011 | Trimbur et al. |
| 2011/0217745 | A1 | 9/2011 | Li et al. |
| 2011/0252696 | A1 | 10/2011 | Franklin et al. |
| 2011/0262970 | A1 | 10/2011 | Li et al. |
| 2011/0314726 | A1 | 12/2011 | Jameel et al. |
| 2012/0028319 | A1 | 2/2012 | Trimbur et al. |
| 2012/0036768 | A1 | 2/2012 | Phillips et al. |
| 2012/0094340 | A1* | 4/2012 | Morgan ................ C11B 13/005 435/134 |
| 2012/0122192 | A1 | 5/2012 | Trimbur et al. |
| 2012/0159838 | A1 | 6/2012 | Malm et al. |
| 2012/0159839 | A1 | 6/2012 | Koskinen et al. |
| 2012/0159840 | A1* | 6/2012 | Koskinen ............. C12N 9/2434 44/307 |
| 2012/0164701 | A1 | 6/2012 | Trimbur et al. |
| 2012/0237980 | A1* | 9/2012 | Hallberg ................ B01D 3/002 435/72 |
| 2012/0288930 | A1 | 11/2012 | Trimbur et al. |
| 2013/0143285 | A1 | 6/2013 | Tolan et al. |
| 2013/0330790 | A1 | 12/2013 | Trimbur et al. |
| 2014/0170716 | A1 | 6/2014 | Trimbur et al. |
| 2014/0234919 | A1 | 8/2014 | Yu et al. |

FOREIGN PATENT DOCUMENTS

| CN | 102171359 A | 8/2011 |
| EP | 1 396 531 A2 | 3/2004 |
| EP | 1 398 364 A1 | 3/2004 |
| EP | 1 741 767 A1 | 1/2007 |
| EP | 1 741 768 A1 | 1/2007 |
| EP | 2 468 857 A1 | 6/2012 |
| EP | 2 468 875 A1 | 6/2012 |
| EP | 2 468 877 A1 | 6/2012 |
| WO | WO 01/32715 A1 | 5/2001 |
| WO | WO 2008/151149 A2 | 12/2008 |

(Continued)

OTHER PUBLICATIONS

Ruan et al. Evaluation of lipid accumulation from lignocellulosic sugars by Mortierella isabellina for biodiesel production. Bioresource Technology (2012), v110, p. 198-205.*

(Continued)

*Primary Examiner* — Sean C. Barron
(74) *Attorney, Agent, or Firm* — Buchanan Ingersoll & Rooney PC

(57) ABSTRACT

The present disclosure relates to a method for obtaining sugar and lignin fractions from lignocellulosic materials and to a method for producing fermentation products using the sugars obtained from the lignocellulose. The present disclosure also relates to a method for improving the sugar yield in the enzymatic hydrolysate by introducing a pre-treatment step of hydrothermal hydrolysis with a delignification step using a cationic compound.

16 Claims, 17 Drawing Sheets

(56) References Cited

FOREIGN PATENT DOCUMENTS

| WO | WO 2010/025455 A2 | 3/2010 |
|---|---|---|
| WO | WO 2010/039783 A2 | 4/2010 |
| WO | WO 2010/060052 A2 | 5/2010 |
| WO | WO 2012/085340 A1 | 6/2012 |
| WO | WO 2013/006755 A2 | 1/2013 |

OTHER PUBLICATIONS

Huang et al. A new pulping process for wheat straw to reduce problems with the discharge of black liquor. Bioresource Technology (2007), v98, p. 2829-2835.*
M. Hubbe. "Polyaluminum Chloride (PAC)" Internet Article (2002), one page.*
Chen et al. Understanding of alkaline pretreatment parameters for corn stover enzymatic saccharification. Biotechnology for Biofuels (2013), v6(8), 10 pages.*
Alkaline. (2011). In the Editors of the American Heritage Dictionaries (Ed.), The American Heritage dictionary of the English language (5th ed.). Boston, MA: Houghton Mifflin. Retrieved from https://search.credoreference.com/content/entry/hmdictenglang/alkaline/0.*
Cheng et al. Evaluation of High Solids Alkaline Pretreatment of Rice Straw. Appl. Biochem Biotechnol (2010), v162, p. 1768-1784. (Year: 2010).*
Rahikainen et al. Inhibition of Enzymatic Hydrolysis by Residual Lignins From Softwood—Study of Enzyme Binding and Inactivation on Lignin-Rich Surface. Biotechnology and Bioengineering (2011), 102(12), 2823-2834. (Year: 2011).*
International Search Report (PCT/ISA/210) dated Feb. 16, 2015, by the Japanese Patent Office as the International Searching Authority for International Application No. PCT/EP2014/077462.
Written Opinion (PCT/ISA/237) dated Feb. 16, 2015, by the Japanese Patent Office as the International Searching Authority for International Application No. PCT/EP2014/077462.
International Search Report (PCT/ISA/210) dated Jan. 28, 2015, by the Japanese Patent Office as the International Searching Authority for International Application No. PCT/EP2014/077464.
Written Opinion (PCT/ISA/237) dated Jan. 28, 2015, by the Japanese Patent Office as the International Searching Authority for International Application No. PCT/EP2014/077464.
International Search Report (PCT/ISA/210) dated Feb. 12, 2015, by the Japanese Patent Office as the International Searching Authority for International Application No. PCT/EP2014/077465.
Written Opinion (PCT/ISA/237) dated Feb. 12, 2015, by the Japanese Patent Office as the International Searching Authority for International Application No. PCT/EP2014/077465.
Barcelos, C.A. et. al., "The Essentialness of Delignification on Enzymatic Hydrolysis of Sugar Cane Bagasse Cellulignin for Second Generation Ethanol Production", Waste and Biomass Valorization, Jun. 21, 2012, pp. 341-346, vol. 4, No. 2. XP055117486.
Muhammad, I. et al., "Effect of Various Pretreatment Conditions on Enzymatic Saccharification", Songklanakarin Journal of Science and Technology, Jul.-Aug. 2011, pp. 397-404, vol. 33, No. 4. XP055117426.
Huang, C. et al., "Microbial Oil Production From Rice Straw Hydrolysate by *Trichosporon fermentans*", Bioresource Technology, Oct. 1, 2009, pp. 4535-4538, vol. 100, No. 19. XP026148880.
Xue-Fang, C. et al., "Microbial Oil Production From Corncob Acid Hydrolysate", Biotechnology Letters, Feb. 16, 2012, pp. 1025-1028, vol. 34, No. 6. XP035047251.
Yu, X. et al., "Oil Production by Oleaginous Yeasts Using the Hydrolysate From Pretreatment of Wheat Straw With Dilute Sulfuric Acid", Bioresource Technology, Feb. 18, 2011, No. 10, pp. 6134-6140, vol. 102. XP028407881.
Ruan, Z. et al., "Evaluation of lipid accumulation from lignocellulosic sugars by *Mortierella isabellina* for biodiesel production", Bioresource Technology, Jan. 28, 2012, pp. 198-205, vol. 110.
Yousuf, A., "Biodiesel from lignocellulosic biomass—Prospects and challenges", Waste Management, Apr. 3, 2012, pp. 2061-2067, vol. 32, No. 11.
Tanaka, M. et al., "Removal of Lignin and Reuse of Cellulases for Continuous Saccharification of Lignocellulos", Biotechnology and Bioengineering, 1988, pp. 897-902, vol. 32.
Harmsen, P. et al., "Literature review of physical and chemical pretreatment processes for lignocellulosic biomass", Wageningen Ur Food and Biobased Research, Sep. 2010, pp. 1-48, retrieved from the internet: http://www.biomassandbioenergy.nl/filesdwnld/Literature%20review_FBR.pdf.
Alvira, P. et al., "Pretreatment technologies for an efficient bioethanol production process based on enzymatic hydrolysis: A review", Bioresource Technology, Dec. 29, 2009, pp. 4851-4861, vol. 101, No. 13.
Huang, HJ et al., "A review of separation technologies in current and future biorefineries", Separation and Purification Technology, Aug. 2008, pp. 1-21, vol. 62, No. 1.
Notification of the First Office Action dated Apr. 23, 2019, by the Chinese Patent Office in corresponding Chinese Patent Application No. 201480067021.3, and an English Translation of the Office Action. (18 pages).

\* cited by examiner

Table 1

| Delignification treatment | Amount of alkaline chemical[a] | pH before treatment[b] | pH after treatment[c] | DM yield[d] | Monomeric sugar yield based on delignified straw DM[e] | Sugar yield based on autohydrolyzed straw DM (%)[f] | Sugar yield based on autohydrolyzed straw carbohydrates (%)[g] |
|---|---|---|---|---|---|---|---|
| NaOH + 2% H₂O₂ solution | 3.3 | 10.2 | 8.5 | 77 | 0.48 | 37.0 | 63.1 |
| Ca(OH)₂ | 3 % saturated solution | 10.30 | 9.3 | 91 | 0.41 | 37.3 | 63.7 |
| Ca(OH)₂ + 1% H₂O₂ solution | 3 % saturated solution | 9.30 | 7.8 | 91 | 0.42 | 38.2 | 65.2 |
| NaOH | 0.85 | 10.0 | 8.8 | 89 | 0.44 | 39.5 | 67.4 |
| AH straw without delignification | 0 | 5.2 | 5.3 | 100 | 0.36 | 36.0 | 61.4 |

[a] % of autohydrolyzed straw on dry matter basis
[b] pH of the liquor before heating
[c] pH of the liquor after heating and filtration of solids
[d] % dry matter left after delignification treatment
[e] ratio of monomeric sugars obtained from enzymatic hydrolysis to dry matter of delignified straw on g/g basis
[f] ratio of sugars obtained from enzymatic hydrolysis to dry matter of autohydrolyzed straw
[g] calculated as the ratio of total amount of monosaccharides released in enzymatic hydrolysis to total amount of monosaccharides released from similar weight of autohydrolyzed straw in acid hydrolysis multiplied with the dry matter yield from the delignification treatment

FIG. 17

METHOD OF PROCESSING LIGNOCELLULOSIC MATERIAL USING A CATIONIC COMPOUND

FIELD OF THE INVENTION

The present invention relates to a method for obtaining sugar and lignin fractions from lignocellulosic materials and to a method for producing single-cell oil using the sugars obtained from the lignocellulose. The method is also related to recycling an alkaline liquid stream obtained from delignification treatment of lignocellulosic material

BACKGROUND OF THE INVENTION

Lignocellulose is the most abundant biopolymer on earth. Lignocellulose is the major structural component of woody plants and non-woody plants such as grass. Lignocellulosic biomass refers to plant biomass that is composed of cellulose, hemicellulose, and lignin. Large amounts of lignocellulosic residues are produced through forestry, timber and pulp and paper industries and agricultural practices (e.g. straw, stover, sugar cane bagasse, chaff, hulls) and many agroindustries. Also municipal waste contain fractions that can be considered as lignocellulose residues, such as paper or cardboard waste, garden waste or waste wood from construction. Lignocellulosic residues, such as agricultural residues, offer highly sustainable, non-food and non-ILUC (indirect land use change), alternative for production of biofuels. In addition, due to high abundance and low price lignocellulosic residues are preferred materials for production of biofuels. In addition, dedicated woody or herbaceous energy crops with biomass productivity have gained interest as biofuel use.

The production of biofuels, especially ethanol, from lignocellulosic materials by microbial fermentations has been studied extensively. The greatest challenge for utilization of lignocellulosics for microbiological production of biofuels or biofuel feedstocks lays in the complexity of the lignocellulose material and in its resistance to biodegradation. In lignocellulose, cellulose (20-50% of plant dry weight) fibers are embedded in covalently bound matrix of hemicellulose (20-40%), pectin (2-20%) and lignin (10-25%) forming very resistant structure for biodegradation.

Further, the sugar residues of hemicellulose contain a varying mixture of hexoses (e.g., glucose, mannose and galactose), and pentoses (e.g., arabinose and xylose) depending on the biomass.

Certain microorganisms can produce lipids from organic molecules, such as sugars derived from lignocellulose. Certain microorganisms, typically yeast, fungi or bacteria, can efficiently convert both C6 and C5 sugars in lignocellulosic materials to oil. Oil produced by heterotrophic microorganisms is often called as single cell oil or microbial oil. Single cell oil production process using heterotrophic microorganisms comprises cultivating microorganisms in aerated bioreactors, allowing cells to accumulate lipids, harvesting lipid-rich cells and recovering oil from cells. Microorganism-based lipids (i.e. single cell oils) can be used as raw materials for production of biofuels such as biodiesel, renewable diesel or bio jet fuel.

The economically feasible production of biofuels from lignocellulosic materials by microbial fermentation requires an efficient conversion of all the main carbohydrate constituents of the lignocellulosic materials to biofuels. On the other hand the economic feasibility of the biofuel production requires that all the main carbohydrate constituents of the lignocellulosic material have to be converted to sugars, which are suitable for microbial fermentation. Generally this means breaking (hydrolyzing) the polymeric structures of hemicellulose and cellulose fractions to obtain monomeric sugars.

The prior art discloses several methods, which aim at production of sugars from lignocellulosic materials and use of sugars in a microbial fermentation process.

Patent publication WO2010039783A1 describes a method for producing fermentable sugars from lignocellulosic materials, in which method the lignin dissolved during alkali treatment is adsorbed to a cationic starch polymer before conducting the cellulosic fraction to an enzymatic hydrolysis treatment. The publication does not include the separation of alkaline delignification liquid after delignification treatment prior to enzymatic hydrolysis to recover lignin from delignification liquid, and to recycle the liquid stream back to delignification treatment after lignin recovery with cationic compound without the the change in pH. In the known method, the adsorbed lignin is not removed from the cellulosic fraction before the enzymatic hydrolysis treatment. According to the teachings of WO2010039783A1 the lignin adsorption enhances the enzymatic hydrolysis treatment.

Patent publication IN217148B discloses a method for separation of lignin from black liquor from a pulp making process with a combination of a flocculant such as a cationic starch polymer and coagulant such as mineral acid with a change in pH to less than pH 6.

One of the major challenges in production of lignocellulosic sugars from lignocellulosic material is to provide a process, which enables cost-efficient production of high quality sugar hydrolysates, which can be used in a subsequent production of fermentation step. The high quality of the sugar hydrolysates means that the amount of impurities such as phenols and acids should be below the concentration, which is toxic to the microorganism used in the fermentation. The cost efficiency requires that the consumption of chemicals used in production of hydrolysates should be kept at low level. This can be achieved for example by recycling of cooking chemicals. The economic feasibility also requires that the quality of the side streams, which are not used as raw material for microbial fermentation, should be as high as possible to enable the valorization of these streams.

State-of-the-art lignocellulose pre-treatment technologies have been designed for anaerobic fermentations (cellulosic ethanol). Microbial oil production differs from anaerobic fermentations since it is aerobic process (requires oxygen). This invention describes a lignocellulose fractionation process that has benefits especially for aerobic bioprocesses, such as microbial oil production. The current invention is, however, also applicable to anaerobic bioprocesses.

SUMMARY OF THE INVENTION

The object of the present invention is to provide a lignocellulose fractionation process, which solves the problems of the prior art processes relating to a low overall sugar yield from the lignocellulosic material and high chemical costs of harvesting the non-carbohydrate products.

Another object of the present invention is to provide a method, which enables production of sugar hydrolysates to be used in production of microbial oil with heterotrophic microorganisms.

Still another object of the present invention is to provide a fractionation process with improved yield and productivity of the enzymatic hydrolysis treatment.

Still another object of the present invention is to provide a more cost efficient and versatile process for recovery and valorization of non-carbohydrate fractions of lignocellulose.

To achieve the above state objects, the invention is characterized by the features defined in the independent claims. Other preferred embodiments are presented in dependent claims.

The invention is based on a finding that lignin dissolved in alkali treatment can be efficiently precipitated with a cationic compound and that after the separation of the precipitate the alkaline liquor can be recycled of the to the alkaline delignification step. The recycling of the alkaline liquor significantly improves the cost efficiency of the alkaline treatment step.

According to the invention, the lignin is precipitated at alkaline pH by using a cationic compound. Furthermore, the lignin precipitation with a cationic compound and separation of the precipitate from the alkaline liqueur can be conducted at alkaline pH without the need to change the pH. This allows efficient recycling of the alkaline agent into the alkaline treatment step of the lignocellulose fractionation method. Since the pH is not changed during the recovery of lignin, the amount of make-up (fresh) alkaline agent to alkaline treatment is lower compared to a case where pH has to be lowered by acidic compounds for the recovery of lignin.

The invention is also based on a surprising finding that by separating lignin prior to enzymatic hydrolysis step by alkali treatment, the efficiency of the enzymatic hydrolysis of the cellulosic fractions and the cost-efficiency of the aerobic fermentation is significantly improved. Cost efficiency aerobic cultivation is improved due to the low amount of inert material (lignin) and inhibitor compounds in the sugar fraction used in aerobic fermentation.

Accordingly, one aspect of the present invention relates to a method for fractionation of a lignocellulosic material, the method comprising
- a) Subjecting the lignocellulosic material to a delignification treatment in the presence of an alkaline delignification agent to produce a mixture comprising a first solid phase and a first liquid phase containing dissolved lignin,
- b) Separating the first solid phase from the first liquid phase,
- c) Introducing a cationic compound into the first liquid phase to produce a mixture comprising a second solid phase and a second liquid phase,
- d) Subjecting the first solid phase to an enzymatic hydrolysis treatment in the presence of enzymes capable of hydrolysing the hemicellulose and cellulose fractions of the first solid phase to produce a mixture comprising a third liquid phase and a third solid phase.
- e) Separating the third liquid phase from the third solid phase A second aspect of the present invention relates to a liquid phase in the form of an enzymatic hydrolysate obtainable by the method of the present invention. The enzymatic hydrolysate may optionally be concentrated.

Thus, a third aspect of the present invention relates to a concentrated sugar hydrolysate obtainable by the method according the method of the present invention.

A further aspect of the relates to a method for production of microbial lipid, the method comprising (i) providing a cultivation medium comprising the a third liquid phase in the form of an enzymatic hydrolysate or concentrated sugar hydrolysate according the present invention, (ii) providing a fermentation broth by inoculating the cultivation medium with an oleaginous microbe, (iii) incubating said medium inoculated with said oleaginous microbe allowing lipid to accumulate, (iv) recovering the lipid from said oleaginous microbe.

BRIEF DESCRIPTION OF THE DRAWINGS

FIG. 17 presents data for Table 1.

Figure 1:
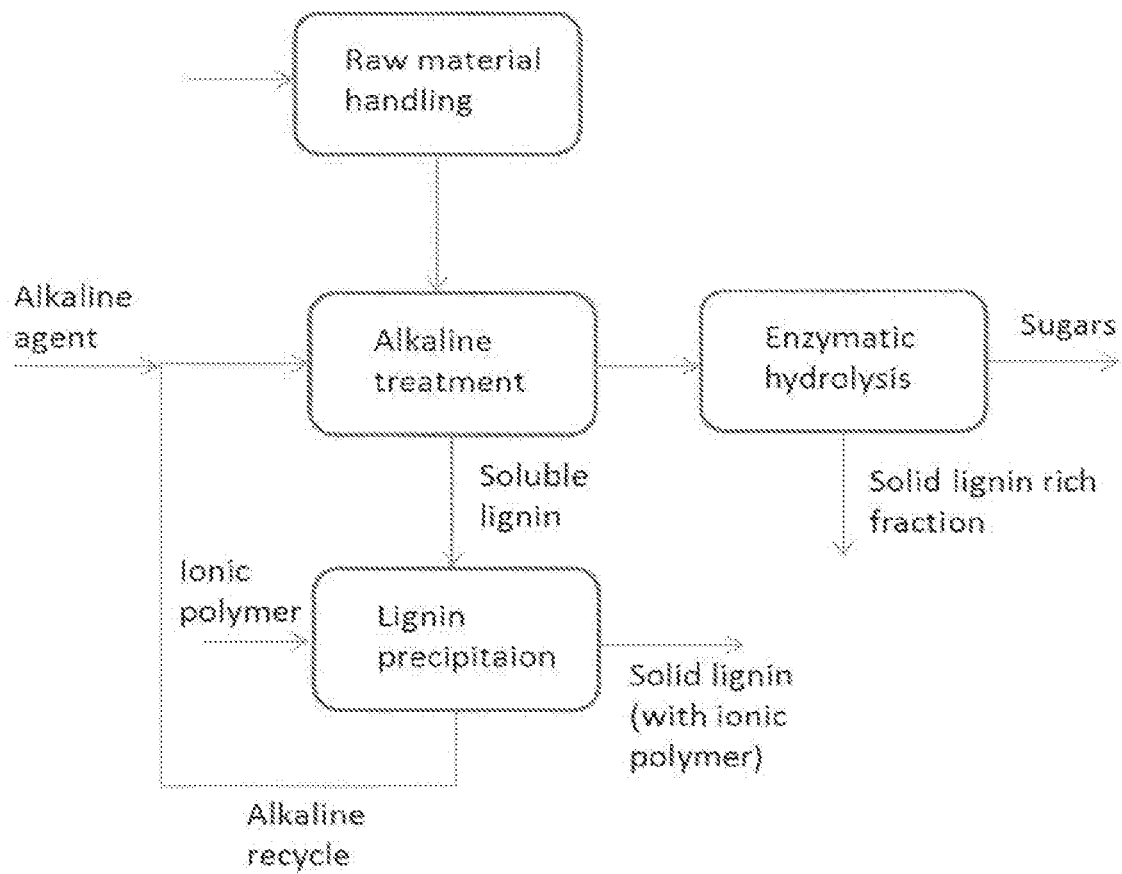
FIG. 1, FIG. 2, and FIG. 3 outline process schemes for treatment of lignocellulosic material according.

Table 1. Comparison of dry matter yield (DM yield) from autohydrolysed straw with different delignification treatments. Sugar yield from enzymatic hydrolysis of delignified straw was dependent on treatment conditions. Sugar yield below is given both based on dry matter of autohydrolyzed straw and based on carbohydrate content of autohydrolyzed straw.

Table 2. Precipitation of lignin from alkaline supernatant by Ca-acetate and by consecutive treatments, first with cationic starch and then with Ca-acetate.

Table 3. Precipitation of lignin from alkaline supernatant by Ca-acetate and by consecutive treatments, first with cationic starch and then with Ca-acetate Table 4. Composition of growth medium before feeds

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

Definitions

Lignocellulosic Material

The terms "lignocellulosic biomass" or "lignocellulosic material" is meant to include but is not limited to woody plants or non-woody, herbaceous plants or other materials containing cellulose and/or hemicellulose: Materials can be agricultural residues (such as wheat straw, rice straw, chaff, hulls, corn stover, sugarcane bagasse, sugar cane tops and leaves), dedicated energy crops (such as switchgrass, *Miscanthus*, *Arundo donax*, reed canary grass, willow, water hyacinth, energy cane, energy sorghum,), wood materials or residues (including sawmill and pulp and/or paper mill residues or fractions, such as hemicellulose, spent sulphite liquor, waste fibre and/or primary sludge), moss or peat, or municipal paper waste. The term lignocellulosic material comprises also low lignin materials, materials such as macroalgae biomass. In addition, the materials comprise also hemicellulose or cellulose fractions from industrial practises. The term lignocellulosic material encompasses any kind of cellulose fraction. The raw materials or certain fractions, such as hemicellulose and/or cellulose, of raw materials from different origin, plant species, or industrial processes can be mixed together and used as raw materials for cultivating microorganism biomass according to this disclosure. Typically the lignin content in lignocellulose is higher than 5%. Lignocellulosic biomass may also contain starch, e.g. in the case of whole plants Hydrolysis The term "hydrolysis" refers here to depolymerisation by addition of water into glycosidic linkages or ester linkages of non-monomeric carbohydrates to sugar oligomers and monomers or carboxylic acids.

Hydrolysate

The terms "hydrolysate" or "hydrolysed material" refers here to material that has undergone hydrolysis.

Severity

The term "severity" refers here to factor, which is calculated by equation 1 and which describes the hydrothermal conditions in terms of temperature and reaction time.

$$S = \text{Log}(R_0),$$

where $R_0 = \int_0^t \exp((T(t)-Tr)/14.7)]dt$ and $Tr$ is the base temperature (100° C.).

Lignocellulose Hydrolysate

The term "lignocellulose hydrolysate" refers here to hydrolysis products of lignocellulose or lignocellulosic material comprising cellulose and/or hemicellulose, oligosaccharides, mono- and/or disaccharides, acetic acid, formic acid, other organic acids, furfural, hydroxymethyl furfural, levulinic acid, phenolic compounds, other hydrolysis and/or degradation products formed from lignin, cellulose, hemicellulose and/or other components of lignocellulose, nitrogen compounds originating from proteins, metals and/or non-hydrolysed or partly hydrolysed fragments of lignocellulose.

Hydrothermal Treatment

In the context of the present invention the term "hydrothermal treatment" refers to heat treatment of aqueous lignocellulose suspension at temperatures exceeding 50° C. Hydrothermal treatment can be carried out under pressure in a pressurized reactor or at atmospheric pressure in a non-pressurized reactor. The pressure in pressurized reactor may be generated by steam obtained from the water when heated up to boiling point or by added pressurized gas phase. Hydrothermal treatment may be carried out in the presence of a catalyst or in the absence of a catalyst. Hydrothermal treatment in the absence of a catalyst (also referred to as "autohydrolysis" or "AH") to hydrolysis of lignocellulosic biomass without added catalyst when aqueous suspension of lignocellulosic biomass is subjected to hydrothermal treatment at temperatures exceeding 120° C. under pressure. "Autohydrolyzed straw" refers here to solid fraction that has been obtained after autohydrolysis. Autohydrolysed straw may have been subjected to washing.

Delignification Treatment

"Delignification treatment" refers here to a treatment that removes non-carbohydrate material such as lignin from lignocellulosic biomass. Delignification treatment also refers to a treatment that removes both non-carbohydrate and carbohydrate material as a mixture from lignocellulosic biomass.

Steam Explosion

In the context of the present invention the term "steam explosion" refers to a treatment, where the material is heated by a high pressure steam (at temperatures between 110° C. and 250° C., typically 140-230° C.) under a pressure with or without the addition of chemicals (such as acids) and the material is held at the temperature for a certain time after which the pressure is released causing an explosive decompression of the material. In this context, steam explosion is applied to lignocellulosic materials, and it typically results in a rupture of the lignocellulose fibers rigid structure, i.e. defibrillation of the cellulose fibre bundles.

Alkaline Delignification Agent

In the context of the present invention the term "alkaline delignification agent" refers to a chemical compound or a mixture of chemical compounds that when added to water give solutions with a hydrogen ion activity lower than that of pure water, i.e., a pH higher than 7.0. Alkaline delignification agent can be selected from a group of compounds comprising but not limited to hydroxides such as LiOH (lithium hydroxide), NaOH (sodium hydroxide), KOH (potassium hydroxide), Ca(OH)$_2$ (calcium hydroxide), NH$_4$OH (ammonium hydroxide), or compounds that can form hydroxide ions in water such as NH$_3$ (ammonia) in liquid or gaseous state, carbonates such as HCO$_3$— (bicarbonate ion), Li$_2$CO$_3$ (lithium carbonate), Na$_2$CO$_3$ (sodium carbonate), K$_2$CO$_3$ (potassium carbonate), sulfides such as Na$_2$S (sodium sulfide), and the corresponding hydrates Alkaline Delignification Treatment In the context of the present invention the term "alkaline delignification treatment refers to treatment of lignocellulose performed in the presence of alkaline delignification agent, pH (starting pH) typically between 10 and 13. In alkaline delignification treatment hydrogen peroxide (H$_2$O$_2$) can be used in combination with alkaline delignification agent.

Cationic Compound

The term "cationic compound" refers to The term "cationic compound" refers to one or more compounds that comprises cationic ions or mixtures thereof that comprises cationic ions. Cationic compounds include but are not limited to compounds comprising cationic group such as quaternary ammonium cation. Cationic compounds comprising quaternary ammonium cation include but are not limited to cationic polymers and oligomers, such as cationic starch, cationic amylose, cationic amylopectin, cationic dextran, cationic lignin oligomers, cationic lignin polymers, cationic peat, or mixtures thereof. Preferential cationic polymers and oligomers have a cationic charge density of 0.5-5 meq/g. Cationic compounds include also, compounds that can form divalent or multivalent cationic ions such as Ca2+ or Mg2+ ions in water. These compounds that can form divalent or multivalent cationic ions include but are not limited to acetates, bicarbonates, bromides, chlorides, formates, hydroxides, and nitrates of the multivalent cationic ions. In a preferred embodiment of the present invention, the method of fractionation uses a cationic starch or aluminium chloride.

Oligomeric Compound

Oligomer and oligomeric compound refer to a compound consisting of less than 15 identical or non-identical linked monomeric units.

Enzymatic Hydrolysis

In the context of the present invention the term "enzymatic hydrolysis" refers to enzymatic treatment of the lignocellulosic material comprising cellulose and/or hemicellulose, oligosaccharides, where enzymes facilitates the hydrolysis of the cellulose and/or hemicellulose, oligosaccharides to obtain mono- and/or disaccharides. Typically the enzymatic hydrolysis treatment of the lignocellulosic material is conducted by subjecting the lignocellulosic material to a mixture of enzymes in the presence of water or a buffer. The mixture of enzymes typically consists of, but is not limited to 1,4-β-glucanases (endoglucanaces and exoglucanases, or endocellulases and exocellulases), 1,4-β-glucosidases (cellobiases) and hemicellulose-degrading enzymes (hemicellulases, xylanases, arabinases etc.).

Microbial Lipid or Lipid

In the context of the present invention "microbial lipid", "lipid" or "intracellular lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as triacylglycerols, diacylglycerols, or monoacylglycerols. Preferred lipids in the present invention are fats, oils, waxes, acylglycerols and fatty acids and their derivatives, in particular triacylglycerols and wax esters. In the context of the present invention the lipids are synthesized by and accumulated in microbes (intracellular lipids). In another embodiment of the invention, lipids are synthetized by and excreted by microbes (extracellular lipids).

In connection of this invention single cell oil is used as synonym for lipids and fat.

The term "acyglycerol" refers to an ester of glycerol and fatty acids. Acylglycerols occur naturally as fats and fatty oils. Examples of acylglycerols include triacylglycerols (TAGs, triglycerides), diacylglycerols (diglycerides) and monoacylglycerols (monoglycerides).

Sugar

In the context of the present invention the term "sugar" refers here to oligomeric, dimeric and monomeric carbohydrates. Particularly, in this application the term sugar refers to water soluble oligomeric, dimeric and monomeric carbohydrates derived from lignocellulosic materials. By the term "polymeric sugars" is meant carbohydrates that are in polymeric form and not typically soluble in water.

Sugar Yield

In the context of the present invention the term "sugar yield" refers here to the yield of oligomeric, dimeric and monomeric carbohydrates from particular materials. Particularly, in this application the term sugar yield refers to the yield of water soluble oligomeric, dimeric and monomeric carbohydrates derived from lignocellulosic materials.

Single Cell Oil Production Process

"Single cell oil production process" refers here to a process, comprising steps of forming or allowing the growth of a lipid synthesizing microorganism and allowing the thus obtained organism mass to produce and/or store (accumulate) lipid, recovering the cells from the liquid phase, and extracting or recovering the lipids from the cells. In certain cases, single cell oil can be also extracellular such as excreted or liberated from cells in culture medium during or after cultivation.

Aerobic Cultivation

The term "aerobic cultivation" or "aerobic fermentation" refers to cultivation where the microorganism utilizes oxygen as terminal electron acceptor for energy generation (i.e. microorganism uses aerobic respiration). Typically in bioreactors, aerobic cultivation is performed by adding oxygen or a gas mixture containing oxygen (typically air), i.e. bioreactor is aerated. When microorganisms use aerobic respiration in cultivation, it can be referred as "cultivation under aerobic conditions". Typically this occurs in aerated bioreactors.

Single Cell Oil Production Process

"Single cell oil production process" refers here to a process, comprising steps of forming or allowing the formation of a lipid synthesizing microorganism and allowing the thus obtained organism mass to produce and/or store (accumulate) lipid, recovering the cells from the liquid phase, and extracting or recovering the lipids from the cells. In certain cases, single cell oil can be also extracellular such as excreted or liberated from cells in culture medium during or after cultivation.

Oleaginous Microbe or Oil Producing Microorganism

The oleaginous microbe (also refer to as oil producing organisms) used in the present invention are selected from the group of bacteria, cyanobacteria, fungi such as yeasts and filamentous fungi, archaea or microalgae. The microorganisms can readily accumulate lipids or have been genetically modified to accumulate lipids or to improve accumulation of lipids.

Preferably organisms that are capable of utilizing C6 and C5 sugars are used. Preferably organisms are yeast, filamentous fungi or bacteria.

In the context of the present invention, the oleaginous microorganism (oleaginous microbe) refers to a microorganism which is capable of accumulating intercellular lipids such that the lipids mounts at least 15% (w/w) of the total biomass (per cell dry weight) of the microbe when it is cultivated under suitable conditions. In a preferred embodiment, the oleaginous microbe is capable of accumulating at least 20% (w/w) of the total biomass of the microbe (per cell dry weight).

Preferred microorganism strains for the purposes of the present invention include, but are not limited to, the species and genera listed below:

According to one embodiment of the invention, the microbe is an oleaginous microbe capable of utilizing sugars derived from lignocellulosic materials. Preferably, oleaginous organisms are capable of utilizing C6 sugars (six carbon sugars, such as glucose, mannose and galactose) and C5 sugars (such as xylose and arabinose) in lignocellulosic hydrolysates. According to one embodiment of the invention, the oleaginous organism is capable of utilizing polymeric or oligomeric carbohydrates in lignocellulose or fractions thereof.

Preferred (filamentous) fungal strains are from species from genera *Aspergillus* such as *Aspergillus oryzae*, *Mortierella* such as *Mortierella isabellina*, *Chaetomium*, *Claviceps*, *Cladosporidium*, *Cunninghamella*, *Emericella*, *Fusarium*, *Glomus*, *Mucor*, *Pseudozyma*, *Pythium*, *Rhizopus*, such as *Rhizopus oryzae*, *Tremella*, *Zygorhynchus*, *Humicola*, *Cladosporium*, *Malbranchea*, *Umbelopsis* such as *Umbelopsis isabellina* and *Ustilago*. Most preferred fungal species are from genera *Aspergillus* and/or *Mortierella*. Preferred fungi are those fungi capable of effectively producing lipids.

Preferred yeast strains are those belonging to species from genera, *Geotrichum*, *Deparyomyces*, *Pachysolen*, *Galactomyces*, *Hansenula*, *Leucosporidium*, *Sporobolomyces*, *Sporidiobolus*, *Waltomyces*, *Cryptococcus*, such as *Cryptococcus curvatus*, *Rhodosporidium*, such as *Rhodosporidium toruloides* or *Rhodosporidium fluviale*, *Rhodotorula*, such as *Rhodotorula glutinis*, *Yarrowia*, such as *Yarrowia lipolytica*, *Candida* such as *Candida curvata*, *Lipomyces* such as *Lipomyces starkeyi* and *Trichosporon* such as *Trichosporon cutaneum* or *Trichosporon pullulans*. Most preferred yeasts are from genera *Lipomyces*, *Rhodosporidium* and *Cryptococcus*. Preferred yeasts are those yeasts capable of producing effectively lipids.

Preferred bacteria are those belonging to the species from genera *Rhodococcus*, *Acinetobacter* and *Streptomyces*. Preferred bacteria are those bacteria capable of producing effectively lipids.

Most preferred algae are microalgae, such as microalgae species from genera comprising, *Brachiomonas*, *Crypthecodinium*, *Chlorella*, *Dunaliella*, *Hantzschia*, *Nannochloris*, *Nannochloropsis*, *Nitzschia*, *Prototheca*, *Scenedesmus*, *Schizochytrium*, *Traustrochytrium* and *Ulkenia*. Preferred microalgae are those microalgae capable of growing heterotrophically and producing effectively lipids. The organisms belonging to the genera *Schizochytrium*, *Thraustochytrium* and *Crypthecodinium* and *Ulkenia* are sometimes called as marine fungi.

According to another embodiment of the invention, the carbohydrates from lignocellulosic biomass are in mainly monomeric form and organisms not capable of utilizing oligomeric or polymeric carbohydrates are used for single cell oil production. Such oil producing organisms are selected from the group of bacteria, cyanobacteria, fungi such as yeasts and filamentous fungi, archaea or microalgae. The microorganisms can readily accumulate lipids or have been genetically modified to accumulate lipids or to improve accumulation of lipids.

Lipid Recovery

"Oil recovery" or "Lipid recovery" or "recovering lipid from an oleaginous microbe" refers to a process, in which the lipid (intracellular lipid) is recovered by mechanical, chemical, thermomechanical or autocatalytic methods or by a combination of these methods from the microorganism cells. Alternatively, "oil recovery" can mean the recovery of extracellularly produced lipids from the cultivation (fermentation) broth.

Lipid Containing Single-Cell Mass

"Lipid-containing single-cell mass" stands for a single-cell mass and cellular mycelium with a lipid content of at least preferably at least 10%, preferably at least 15% (w/w) or more of dry matter of the microorganism biomass.

Residual Cell Mass

In the context of the present invention "residual cell mass" refers to a solid, semi-solid or flowing material fraction, which contains microorganisms treated for the recovery of intracellular lipids.

Biofuel

In the context of the present invention "biofuel" refers to solid, liquid or gaseous fuel mainly derived from biomass or bio waste and is different from fossil fuels, which are derived from the organic remains of prehistoric plants and animals.

According to EU directive 2003/30/EU "biodiesel" refers to a methyl-ester produced from vegetable oil or animal oil, of diesel quality to be used as biofuel. More broadly, biodiesel refers to long-chain alkyl esters, such as methyl, ethyl or propyl-esters, from vegetable oil or animal oil of diesel quality. Biodiesel can also be produced from microorganism lipids, whereby microorganism lipid can originate from a bacterium, a fungus (yeast or a mold), an algae or another microorganism.

Renewable Diesel

"Renewable diesel" refers to a fuel which is produced by a hydrogen treatment of lipids of an animal, vegetable or microorganism origin, or their mixtures, whereby microorganism lipid can originate from a bacterium, a fungus (yeast or a filamentous fungus), an algae or another microorganism. Renewable diesel can be produced also from waxes derived from biomass by gasification and Fischer-Tropsch synthesis. Optionally, in addition to hydrogen treatment, isomerization or other processing steps can be performed. Renewable diesel process can also be used to produce jet fuel and/or gasoline. The production of renewable diesel has been described in patent publications EP 1396531, EP1398364, EP 1741767 and EP1741768.

Biodiesel or renewable diesel may be blended with fossil fuels. Suitable additives, such as preservatives and antioxidants may be added to the fuel product.

Lubricant

"Lubricant" refers to a substance, such as grease, lipid or oil that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demulsifiers, antifoaming agents, co-solvents, and lubricity additives (see for example U.S. Pat. No. 7,691,792). Base oil for lubricant can originate from mineral oil, vegetable oil, animal oil or from a bacterium, fungi (yeast or a filamentous fungus), an algae or another microorganism. Base oil can also originate from waxes derived from biomass by gasification and Fischer-Tropsch synthesis. Viscosity index is used to characterise base oil. Typically high viscosity index is preferred.

The lipids produced according with the method described in this invention can be used as feedstock for the production of biodiesel, renewable diesel, jet fuel or gasoline. Biodiesel consists of fatty acid methyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogen deoxygenation, hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications.

Lipids produced with the method can also be used as base oils for lubricants (lubrication oils) or as a starting material for production of base oils for lubricants Dry Matter "DM" or "dry weight" refers here to dry matter and is a measurement of the mass of a material when it has been subjected to a treatment that essentially removes water from the material (i.e. material is completely dried).

Consistency

"Consistency" refers here to the ratio of dry weight of solids to total weight of suspension.

Method for Fractionation of a Lignocellulosic Material

The present invention provides a method for fractionation of a lignocellulosic material for obtaining cellulosic carbohydrate material separated from a substantial part of the lignin has been removed. Optionally the method also provides a fraction comprising hemicellulosic sugars. The method further provides fractions of concentrated lignin. The fraction comprising the cellulosic carbohydrate material obtained from the lignocellulosic material may be used for the preparation of a cultivation medium for the production of microbial lipid such as described herein, optionally the fraction of comprising the carbohydrate material is combined with the a fraction comprising hemicellulosic sugars in a cultivation for production of microbial lipids.

In a first aspect the present invention relates to a method for fractionation of a lignocellulosic material, the method comprising
a) Subjecting the lignocellulosic material to a delignification treatment in the presence of an alkaline delignification agent to produce a mixture comprising a first solid phase and a first liquid phase containing dissolved lignin,
b) Separating the first solid phase from the first liquid phase,
c) Introducing a cationic compound into the first liquid phase to produce a mixture comprising a second solid phase and a second liquid phase,
d) Subjecting the first solid phase to an enzymatic hydrolysis treatment in the presence of enzymes capable of hydrolyzing the hemicellulose and cellulose fractions of the first solid phase to produce a mixture comprising a third liquid phase in the form of an enzymatic hydrolysate and a third solid phase.
e) Separating the third liquid phase from the third solid phase The inventors have discovered that by combining the alkaline delignification step with the subsequent application of a cationic compound, the solubilised lignin may be removed allowing the liquid phase of the material to be re-cycled without a step of precipitating the lignin by lowering the pH.

In a preferred embodiment of the present invention, the second liquid phase is separated from the second solid phase and the second liquid phase is recycled to step a). By re-cycling the second liquid phase and thus conducting one or further rounds of steps a) to e) further lignin may be removed from the liquid phase. Thus, the material may be subject two repeated cycles of alkaline delignification (solubilised lignin) followed by treatment with the cationic compound (removing the solubilised lignin) before the cellulosic sugars are subjected to enzymatic hydrolysis.

Delignification Step Using an Alkaline Delignification Agent

In step a) of the method of fractionation of the lignocellulosic material, the first solid phase (comprising lignocellulosic material optionally from which the hemicellulosic material has been partly removed) is subjected to a step of alkaline delignification, wherein at least part of the lignin is solubilised. The alkaline delignification is performed by subjecting the lignocellulosic material (optionally from which the hemicellulosic material has been partly removed) to an alkaline delignification agent.

The alkali treatment is typically conducted by preparing a suspension comprising lignocellulose material (optionally hydrothermally treated or autohydrolyzed), aqueous liquid, and one or more alkaline chemicals, or mixtures thereof to give pH of the suspension above pH 7. Preferably alkaline chemical is added to an amount to give pH of suspension between 10 and 13.

The alkaline suspension is kept at temperatures where suspension contains at least one liquid phase. The incubation is not limited to any certain temperature but can be conducted at wide temperature range isothermally or non-isothermally. Incubation is preferably carried out at temperatures from 25° C. to 160° C., more preferably 25 to 120° C.

Agitation is optionally conducted to increase efficacy of heat transfer during incubation. Treatment time is selected according to intended degree of dissolution material. Preferably treatment time is from half an hour to twenty hours.

After reaction time the liquid phase and solid phase are separated by using any method such as but not limited to filtration, e.g. pressure filtration or screw press. Solid phase is used for enzymatic hydrolysis to release sugars for further use such as microbial oil production. Liquid phase can be treated to precipitate lignin, such as by acid treatment and precipitated lignin can be separated by any method.

In one embodiment of the present invention, the alkaline delignification agent is selected from a group consisting of sodium hydroxide, sodium carbonate, potassium hydroxide, potassium carbonate, calcium hydroxide, and calcium carbonate, lithium hydroxide, lithium carbonate, ammonium hydroxide, ammonia, sodium sulphide, and the corresponding hydrates. In a preferred embodiment, the alkaline delignification agent is sodium hydroxide. In a preferred embodiment, the alkaline delignification agent is sodium carbonate.

According to yet another embodiment of the invention, the delignification of lignocellulosic material is performed with ammonium as delignification chemical. According to one embodiment of the invention, ammonium fibre expansion (AFEX) or ammonia As mentioned above, the inventors have surprisingly discovered that the alkaline delignification can be effectively done without the excessive application of alkaline delignification agent if the lignocellulosic material is subject to a hydrothermal treatment, such as autohydrolysis, prior to the alkaline delignification. The hydrothermal treatment results in decreased acidity of solid fraction (comprising cellulose, lignin and residual hemicellulose). Therefore, in the alkaline delignification step less alkaline agent is needed compared to the situation when hydrothermal treatment is not performed. Therefore, alkaline treatment after hydrothermal treatment can be performed at lower pH compared to the situation without autohydrolysis. Thus, hydrothermal treatment is beneficial prior to alkaline treatment of lignocellulosic material. One advantage of applying lower amounts of the alkaline delignification agent is that less sugar is lost in the alkaline delignification step compared to a similar treatment conducted in the presence of high amounts of the alkaline delignification agent.

Accordingly, in a preferred embodiment of the present invention, the concentration of delignification agent is from 0.1 to 10 wt %-, more preferably 0.1-4 wt-% based on the amount of lignocellulosic material on dry matter basis. In a further embodiment, the alkaline delignification agent is added to the lignocellulosic material to obtain a suspension having a pH of above 7, preferably between 10 and 13.

In a further embodiment, the delignification treatment is conducted at a temperature of above 25, preferably between 30 and 160° C.

Lignin Recovery Step Using a Cationic Compound

In step b) of the method for fractionation of the lignocellulosic material, the liquor obtained from the product of the alkaline delignification (by separating the mixture of the first solid phase and the first liquid phase) is subjected to a treatment with a cationic compound in order to remove lignin from the material. The cationic compound captures solubilized lignin in the liquid phase (first liquid phase) obtained from separating the product of the alkaline delignification.

The alkaline delignification liquor obtained from alkaline delignification treatment comprises organic and inorganic material such as lignin and other alkali-soluble material. Said alkaline solution (alkaline delignification liquor) has acidity of 7>pH<14. One or more cationic compounds are added to the alkaline solution at dosage sufficient to precipitate the previously soluble organic material. Accordingly, the precipitation is achieved without acidification of the alkaline solution so that pH of the alkaline solution remains essentially unchanged.

Precipitated solid fraction is separated from the alkaline solution by conventional means thereby producing "clarified alkaline solution" and a precipitated solid fraction comprising precipitated organic material and the cationic substance. The precipitated solid fraction can be used as such or further treated to recover the cationic substances. Preferably, the separated lignin can be used for value added applications compared to combustion value. Optionally, the separated lignin fraction is washed.

The clarified alkaline solution is recycled to alkaline treatment step, and the produced alkaline delignification liquor is again precipitated as described above. Optionally, the clarified alkaline solution is mixed with fresh alkali and/or liquid to replace the amounts consumed in the alkaline treatment. The process is repeated until the alkaline delignification liquor is saturated with non-precipitated substances.

In one embodiment of the present invention, the cationic compound is selected from a group comprising cationic polymers and oligomers such as cationic starch polysaccharides, cationic amylose, cationic amylopectin, cationic dextran, cationic lignin oligomers, cationic lignin polymers, cationic peat, or mixtures thereof. In another preferred embodiment, the cationic compound is a cationic starch polymer.

In a further embodiment, the cationic polymers and oligomers have a cationic charge density of 0.5-5 meq/g.

In one embodiment, the cationic compound is an elemental cationic ion selected from the group comprising alkaline earth metals and bivalent and trivalent cations of iron (Fe). In another embodiment, the cationic ion can be derived from compounds such as $AlCl_3$ aluminum chloride, $Ba(C_2H_3O_2)_2$ barium acetate, $Ba(HCO_3)_2$ barium bicarbonate, $BaBr_2$ barium bromide, $BaCl_2$ barium chloride, $Ba(HCO_2)_2$ barium formate, $(Ba(OH)_2$ barium hydroxide), $Ba(NO_3)_2$ barium nitrate, $Ca(C_2H_3O_2)_2$ calcium acetate, $Ca(HCO_3)_2$ calcium bicarbonate, $CaBr_2$ calcium bromide, $CaCl_2$ calcium chloride, $Ca(HCO_2)_2$ calcium formate, $(Ca(OH)_2$ calcium hydroxide), $Ca(NO_3)_2$ calcium nitrate, $Mg(C_2H_3O_2)_2$ magnesium acetate, $Mg(HCO_3)_2$ magnesium bicarbonate, $MgBr_2$ magnesium bromide, $MgCl_2$ magnesium chloride, $Mg(HCO_2)_2$ magnesium formate, $(Mg(OH)_2$ magnesium hydroxide), $Mg(NO_3)_2$ magnesium nitrate, $Fe(C_2H_3O_2)_2$ iron acetate, $FeCl_3$ ferric chloride, and the corresponding hydrates. In a preferred embodiment, the amount of cationic compound is 0.001-0.25 g/g based on the dry matter content of the first liquid phase. In another preferred embodiment, the cationic compound is aluminium chloride.

In one embodiment of the present invention, a mixture of cationic compounds is used by the method, such as a mixture of cationic polymers, a mixture of cationic ions or a mixture of cationic ion and cationic polymers, such as a mixture of cationic compound, wherein the mixture comprises or consist of a cationic starch polymer and aluminium chloride.

Thus, as mentioned above, the second liquid phase still comprising carbohydrates may be thus be recycled and introduced in step a) and subjected to another round of alkaline delignification step optionally followed by a treatment with a cationic compound (as illustrated in FIG. 1). The re-cycling of the second liquid phase may done without the necessary addition of alkaline delignification agent, unlike the situation where the solubilised lignin was precipitated with acid instead of the application of a cationic compound.

Thus, In a further embodiment, the second liquid phase is separated from the second solid phase and the second liquid phase is recycled to step a).

According to the invention, the lignin can be precipitated from the alkaline delignification liqueur without change of pH by cationic compounds and the clarified alkaline delignification liquor (after removal) of lignin precipitate can be recycled to alkaline delignification step. This is beneficial since the amount of make-up (fresh) alkaline agent to alkaline treatment is lower compared to a case where pH has to be lowered by acidic compounds for the recovery of lignin.

Figure 2:
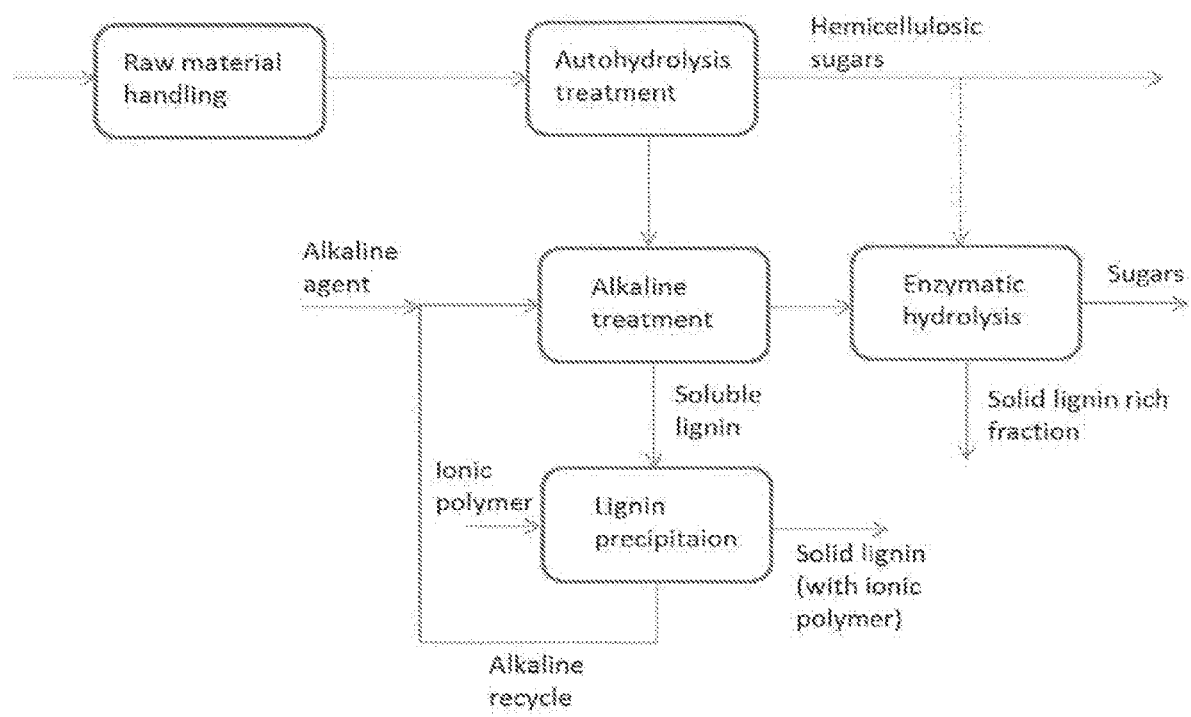
Figure 3:
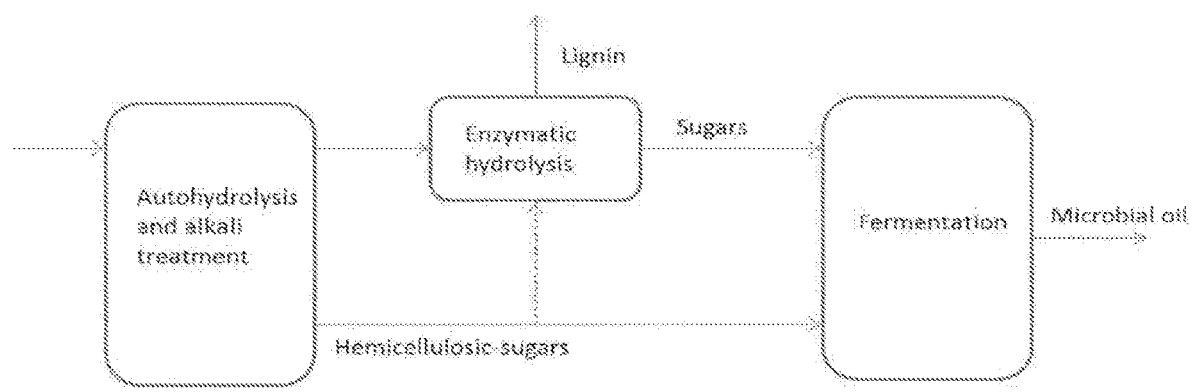
Figure 4:
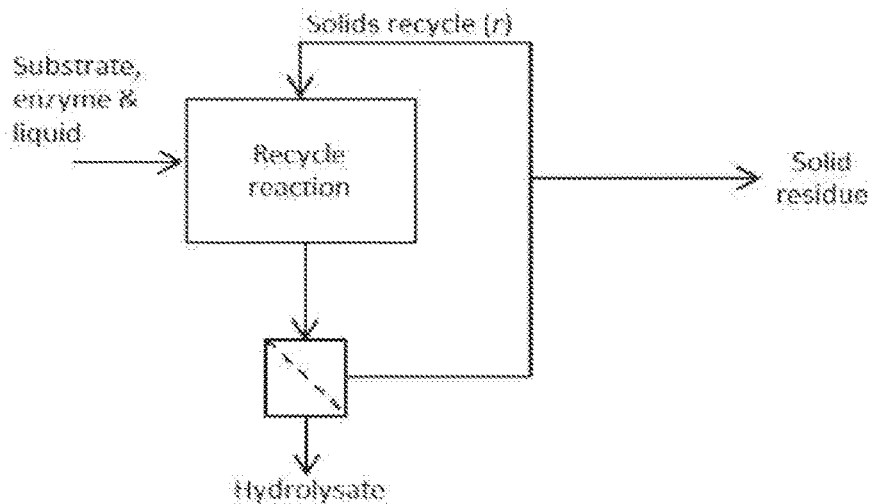
FIG. 4 outlines the process for the enzymatic hydrolysis according to the embodiments of the invention.
Figure 4:
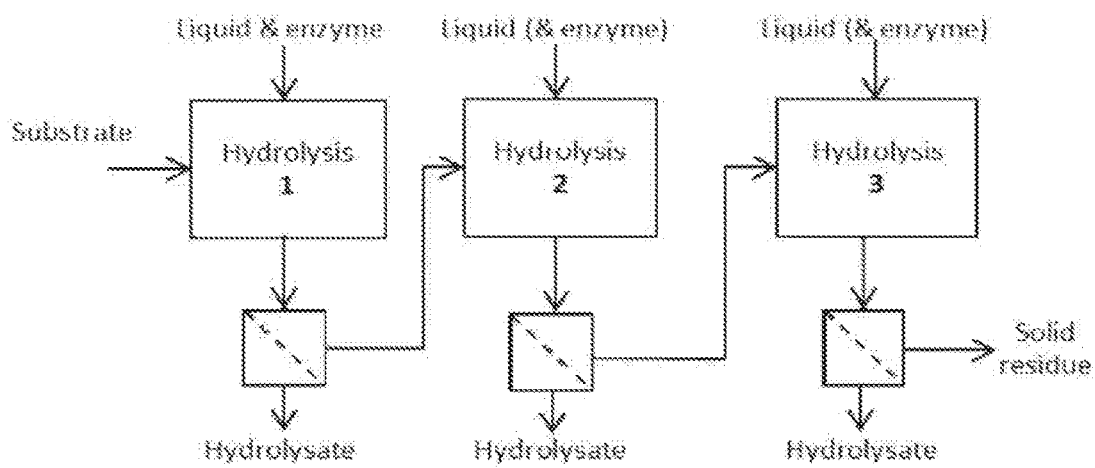

Optional Step of Partially Removing the Hemicellulosic Sugars from the Lignocellulosic Material Before Alkaline Delignification The method for fractionation of the lignocellulosic material may optionally include a step wherein hemicellulose is at least partially removed from the lignocellulosic material to produce a liquid phase comprising the hemicellulose and solid phase of lignocellulosic material, which is introduced in step a) of the method (as illustrated in FIG. 2).

Thus in one embodiment, the lignocellulosic material is subjected to a treatment, wherein hemicellulose is at least partially removed from the lignocellulosic material as an aqueous hemicellulose hydrolysate lignocellulosic material is subjected to step a). In a further embodiment, at least part of the aqueous hemicellulosic hydrolysate is combined with the first solid phase and subjected to enzymatic hydrolysis treatment.

In this optional step of the fractionation method, the hemicelluloses are at least partly dissolved and separated in a liquid phase comprising the hemicelluloses.

It follows that the lignocellulose hydrolysate obtained by the method of the present invention may be obtained by one or more treatments of the lignocellulose or lignocellulosic material including hydrolysis (hydrothermal treatment and/or autohydrolysis), steam explosion with or without addition of acids, one or more step of delignification, before the lignocellulosic material is subjected to the alkaline delignification agent in the alkaline delignification step.

In one embodiment of the present invention, the hemicellulose is at least partly removed from the lignocellulosic material by hydrothermal treatment. In a second embodiment, the hydrothermal treatment is conducted at a temperature of between 100 and 250° C., preferably between 140 and 240° C., and most preferably between 140 and 200° C. The intensification of the hydrothermal treatment may be expressed in terms of severity, the term which is defined herein. In a preferred embodiment, the hydrothermal treatment is conducted in a conditions corresponding to severity of between 2.0 and 4.5, more preferably between 3.0 and 4.1, and most preferably between 3.5 and 4.0.

In another embodiment of the present invention, the hemicellulose is at least partly removed from the lignocellulosic material by autohydrolysis treatment. The autohydrolysis is typically performed at 5-60% dry matter content, at temperatures between 140 and 240 C for 1-120 min without addition of acidic compounds resulting in dissolving of 5- to 40% of dry matter content in lignocellulosic material including hemicellulosic carbohydrates. Typically autohydrolysis dissolves from 30 to 100% of hemicellulosic carbohydrates from lignocellulosic material, preferably more >50%, more preferably >70%, more preferably >80%, even more preferably >90%. The dissolved hemicellulose carbohydrates are at least partly in oligomeric form. More typically, the autohydrolysis is performed at 10-50% dry matter content at 160-220 C, depending on the lignocellulosic raw material. After autohydrolysis, the solid and liquid phases are separated by any method, such as filtration, e.g. pressure filtration, or by a screw press. The solid fraction may be washed to remove dissolved hemicellulose from solid phase.

According to yet another embodiment of the invention, the lignocellulosic material is subjected to a steam or steam explosion with or without addition of acidic compounds, in general at temperatures between 110 and 250° C., more typically at temperatures between 140 and 230° C. The treatment results in a dissolving of hemicellulosic carbohydrates. Optionally, the solid material from steam explosion is washed to recover dissolved hemicellulosic carbohydrates.

In one embodiment, the lignocellulosic material, from which at least part of the hemicellulose is removed, is subjected to a steam explosion before it is introduced in step a). In another embodiment of the present invention, the lignocellulosic material is first subjected to hydrothermal treatment followed by a step of steam explosion. In another embodiment, the solid phase obtained hydrothermal treatment and/or autohydrolysis the is subjected to a steam explosion before the delignification treatment in the presence of the alkaline delignification agent According to the invention, it was surprisingly discovered that the lignocellulose treatment method which includes both treatment step where hemicellulosic sugars become at least partly dissolved (such as autohydrolysis) and treatment step of alkaline delignification (such as treatment with NaOH) allows high overall (total) sugar yield in the process. The high overall sugar yield is beneficial for cost-efficiency of microbial processes such as production of single cell oil.

Enzymatic Hydrolysis of Delignification Product

In step d) of the method of fractionation of the lignocellulosic material, the first solid phase obtained from the step of fractionation using a cationic compound is further subjected to enzymatic hydrolysis. In an alternative embodiment, where the substantial part of the lignin has been removed by repeatedly steps of alkaline delignification and subsequent cationic compound treatment, the second liquid phase may be used in a enzymatic hydrolysis to obtain the third liquid phase comprising the cellulosic sugars.

Enzymatic Hydrolysis

Enzymatic hydrolysis consists of incubation of pretreated straw or other substrate or raw material, with a mixture of enzymes, which typically consists of, but is not limited to 1,4-β-glucanases (endoglucanaces and exoglucanases, or endocellulases and exocellulases), 1,4-β-glucosidases (cellobiases) and hemicellulose-degrading enzymes (hemicellulases, xylanases, arabinases etc.). The enzymes may or may not be commercial enzyme products. The fractionated (pretreated) lignocellulosic material is mixed with water or buffer solution and the enzyme mixture at appropriate proportions. Additives, such as polyethylene glycol, detergents or other surface active agents, or proteins may or may not be added to the reaction. Any proportion of solids in the suspension (or "consistency") may be used, preferably 10-35%, or particularly 15-25%. The pH of the slurry is adjusted according to the optimal conditions for the used enzyme mixture. The pH adjustment is performed before and/or during the addition of enzyme by adding acid or base at a suitable concentration, for example H2SO4, HCl, HNO3, NaOH, NH3 or other acid or base. Further pH adjustment may or may not be performed after the addition of enzymes and during hydrolysis.

A constant temperature is maintained during the hydrolysis, according to the optimal conditions of the enzyme mixture, often 40-60° C., or particularly 50° C. The pretreated straw, water and/or buffer solution and other constituents of the hydrolysis suspension may or may not be preheated to the reaction temperature before they are added to the suspension. The suspension is agitated during the reaction by stirring, shaking, free falling or by other means of agitation.

In one embodiment of the present invention, the enzymatic hydrolysis treatment of the lignocellulosic material is conducted by subjecting the lignocellulosic material to a mixture of enzymes in the presence of water or a buffer. The mixture of enzymes typically consists of, but is not limited to 1,4-β-glucanases (endoglucanaces and exoglucanases, or endocellulases and exocellulases), 1,4-β-glucosidases (cellobiases) and hemicellulose-degrading enzymes (hemicellulases, xylanases, arabinases etc.).

By the subjecting the first solid phase obtained from the alkaline delignification step to enzymatic hydrolysis, further lignin is removed from material in the form of solid lignin (third solid phase). The liquid phase obtained from the enzymatic hydrolysis comprises the sugars releases from the material. The third liquid phase is also referred to as the enzymatic hydrolysate, which may be used for the production of microbial lipids.

Part of the hemi-cellulosic sugars, which are optionally separated from the material, by for example by hydrothermal treatment or autohydrolysis), may be introduced into the system and subjected to enzymatic hydrolysis together with the solid phase material obtained from the alkaline delignification step.

Thus at least part of the separated hemicellulose (liquid phase) may be added to and mixed with solid phase of the alkaline delignification step (the first solid phase) before this mixture is subjecting to the enzymatic hydrolysis treatment of step d). Thus, in one embodiment of the invention, at least part of the first liquid phase is combined with the second solid phase and subjected to enzymatic hydrolysis treatment.

In one embodiment, the enzymatic hydrolysis is conducted as a batch hydrolysis.

Batch Hydrolysis

Batch hydrolysis refers to a hydrolysis reaction, where the reaction constituents are mixed to form a suspension or a slurry or a paste, and incubated for an appropriate period of time, after which the solids are separated by filtration, centrifugation or other means of separation and a liquid stream of soluble sugars, including glucose, xylose arabinose, galactose, mannose and others, and oligomers thereof, is acquired. Reaction constituents or other substances may or may not be added during the reaction. However, no liquid stream is separated from the slurry before the end of the reaction.

A batch reaction may also be performed as a continuous process. In a continuous batch hydrolysis, a constant stream of pre-treated straw, liquid, enzymes, pH-adjustment agents and other reaction constituents is fed to the reactor while simultaneously a constant stream of slurry is removed from the reactor, from which the liquid stream is separated. In a continuous batch hydrolysis, the reactor may or may not be subdivided into two or more reactors in series, through which the slurry flows constantly, particularly in order to improve the retention time distribution of the raw material. Conceptually, the solid material is separated from liquid only after the reaction and no separation takes place during the reaction. Therefore no separation takes place for the outflowing slurry from other reactors except the slurry from the last reactor and, accordingly, no other separate liquid stream is removed from the slurry, than the liquid stream from the separation of the final outflowing slurry. However, additional feed of reaction constituents may take place at any point of the process. If separation of liquid takes place between two reactors, the reactors should be defined as separate reaction steps and the hydrolysis process should be defined as a sequential (stepwise) hydrolysis.

In a second embodiment of the present invention, the enzymatic hydrolysis is conducted as a sequential hydrolysis.

Sequential Hydrolysis

Sequential hydrolysis, also known as stepwise hydrolysis, or two-stage, three-stage or multi-stage hydrolysis, etc., consists of a sequence of batch reactions in series, where between the batch reactions, a liquid stream is separated from the slurry and the concentrated solid stream is fed to the next batch reaction and mixed with fresh water and/or buffer solution. Addition of fresh enzymes and other reaction constituents may or may not take place into the second, third, or latter reaction. The reaction time may be equal or different in the subsequent reaction steps.

Similarly as described for batch reactions, the sequential hydrolysis may be performed as a continuous process and the singe reaction steps of the sequential hydrolysis may be subdivided into separate reactors in series, through which the slurry flows constantly. Separation of liquid and addition of fresh liquid may or may not take place between the reactors. Conceptually, if liquid is separated and the liquid is or is not replaced by fresh liquid between two reactors, the reactors should be defined as separate reaction steps.

In yet a further embodiment, the enzymatic hydrolysis is conducted as a solids-recycle hydrolysis.

Recycling of Residual Solids in Enzymatic Hydrolysis (or "Solids-Recycling")

Figure 5:
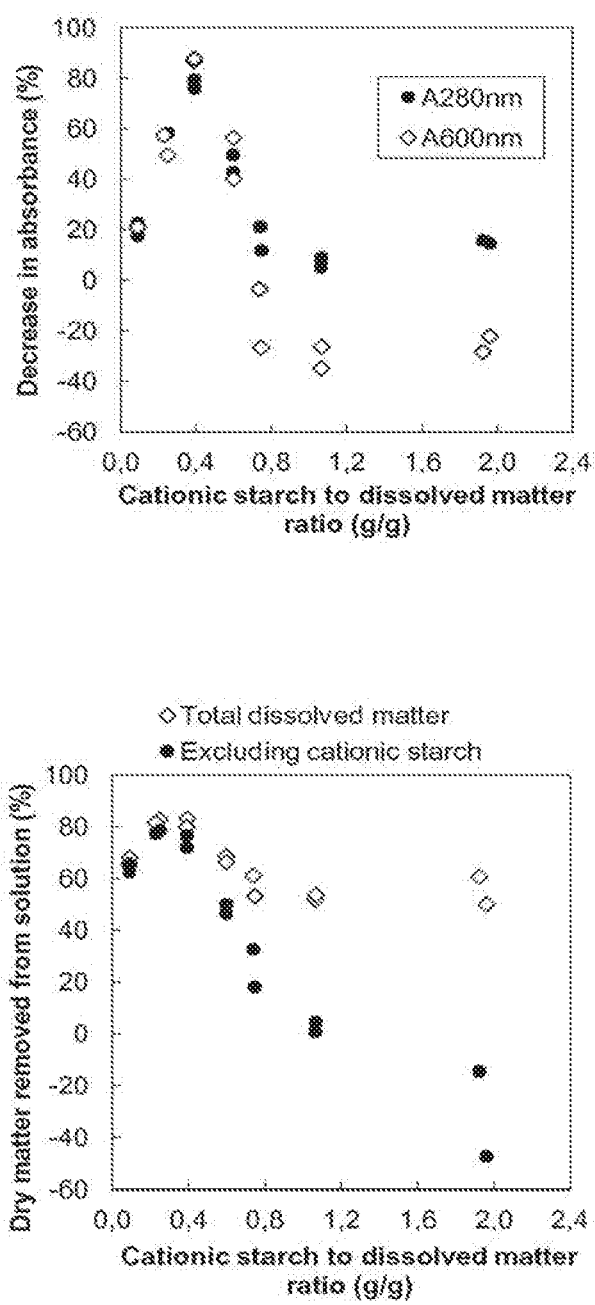
FIG. 5 presents the effect of cationic starch dosage on percentage decrease in absorbance at 280 nm and 600 nm after 4 h incubation of NaOH delignification solution from Example 5 at room temperature.

A hydrolysis process with recycling of the residual solids, or "solids-recycling", includes a hydrolysis reaction, after which a liquid stream is separated from the slurry and a proportion of the concentrated solid stream is recycled back to the same reactor (FIG. 5). The proportion of recycled residual solids is called the recycle rate and denoted by r in FIG. 5 and in Eq. 2 & 3. At a constant raw material feed rate, the solids-recycling extends the reaction time of the solid material according to a geometrical series, presented in Eq. 2, where to is the average reaction time of the solids after n subsequent recycle reactions, t0 is the reaction time of a single reaction, or the retention time of the slurry in the reactor, and r is the recycle rate. Eventually, a recycle process at constant feed and recycle rates and a constant retention time will reach a steady state, at which the average reaction time of the solid material may be calculated from Eq. 3.

$$t_n = \sum_{i=0}^{n-1} t_0 r^i = t_0 \frac{1-r^n}{1-r} \qquad (2)$$

$$t_{Std} = \sum_{i=0}^{\infty} t_0 r^i = \frac{t_0}{1-r} \qquad (3)$$

For example, 50% recycle rate in a 24 h reaction, the average reaction time of the solids will be 48 h at steady state.

The recycle reaction may be performed as a batch reaction, after which solids-recycling takes place, or as a continuous process, where the process constituents are constantly fed to the reactor, a constant outflow of slurry takes place and the outflowing slurry is separated to a liquid and a concentrated residual solid stream and a constant flow of residual solids is recycled back to the reactor. The recycle reaction may or may not be subdivided into separate reactors in series in order to improve the residence time distribution and separation of liquid from or after these reactors and additional feed of process constituents into these reactors may or may not take place. Additional sequential reaction steps may or may not be included after or before or during the solids-recycling reaction.

The hemicellulosic material optionally obtained by subjecting the lignocellulosic material to hydrothermal treatment or autohydrolysis may be at re-introduced (at least partly) at the enzymatic hydrolysis step. Accordingly, in one embodiment of the present invention, at least part of the aqueous hemicellulosic hydrolysate is combined with the first solid phase and subjected to the enzymatic hydrolysis treatment.

The liquid enzymatic hydrolysate obtained in step d) may be subject to a step of concentrating the hydrolysate to obtain a concentrated, such as by evaporation, hydrolysate in order to obtain a fraction having a higher concentration of cellulosic carbohydrates.

Thus, in one embodiment the method according of the invention includes further comprising a step of concentrating the third liquid phase. Preferably, the concentrating of third liquid phase is done by evaporation.

Liquid Enzymatic Hydrolysate (Third Liquid Phase)

The liquid phase (the enzymatic hydrolysate) obtained in step d) of the method of the invention comprises sugars release from the starting material provided in step a) of the method or in the optional prior hydrothermal treatment and/or autohydrolysis step of the method. The liquids phase comprising the sugars may be used in the preparation of a cultivation medium, such as cultivation for use in a method for producing microbial lipids as described herein.

Accordingly, a second aspect of the present invention relates to a liquid phase in the form of an enzymatic hydrolysate obtainable by the method of the present invention (the third liquid phase).

Alternatively, the liquid phase the enzymatic hydrolysate may be concentrated to obtained liquor having a higher concentration of sugars. Thus, a further aspect of the present invention provides a concentrated sugar hydrolysate obtainable by the method of the present invention.

The hemicellulosic hydrolysate from first liquid phase (comprising hemicellulosic sugar monomers) and enzymatic hydrolysate, the third liquid phase (comprising cellulosic sugars) can be used in cultivation broth alone or mixed together as carbon sources for production of single cell oil.

Method for Production of Microbial Lipid

A further aspect of the present invention relates to a method for production of microbial lipid, the method comprising
  (i) providing a cultivation medium comprising the liquid in the form of an enzymatic hydrolysate obtained by method for fractionation of a lignocellulosic material (the third liquid phase) or the concentrated sugar hydrolysate of the present invention,
  (ii) providing a fermentation broth by inoculating the cultivation medium with an oleaginous microbe,
  (iii) incubating said medium inoculated with said oleaginous microbe allowing lipid to accumulate,
  (iv) recovering the lipid from said oleaginous microbe.

The method of the invention is also referred to as a single cell oil production process. The method of the present invention may be part of process for productions of biofuels as described herein, where the oil or at least part of the oil provided in the form of microbial oil by the method described herein.

According to preferred embodiment of the invention the cultivation medium comprises lignocellulosic sugars derived from cellulose and/or hemicellulose. According to the invention, both hemicellulose and/or cellulose fractions of lignocellulosic biomass are used as raw materials for microbial oil production (single cell oil) in the same process (bioreactor system). The process uses preferably oleaginous microbe that are capable of utilizing both C6 (e.g. glucose, mannose, galactose) and C5 (e.g. xylose, arabinose) sugars.

According to another embodiment of the invention, the cultivation medium comprises hemicellulosic sugars derived from lignocellulose. According to yet another embodiment of the invention, the hemicellulosic sugars are at least partly in oligomeric form when fed to a single cell oil production process.

In a preferred embodiment of the present invention the method for production of microbial lipid according to the preceding claim, the method comprising
  a) Subjecting the lignocellulosic material to a delignification treatment in the presence of an alkaline delignification agent to produce a mixture comprising a first solid phase and a first liquid phase containing dissolved lignin,
  b) Separating the first solid phase from the first liquid phase,
  c) Introducing a cationic compound into the first liquid phase to produce a mixture comprising a second solid phase and a second liquid phase,
  d) Subjecting the first solid phase to an enzymatic hydrolysis treatment to hydrolyze the hemicellulose and cellulose fractions of the first solid phase to produce a mixture comprising a third liquid phase in the form of an enzymatic hydrolysate and a third solid phase comprising lignin,
  (i) providing a cultivation medium comprising the third liquid phase in the form of an enzymatic hydrolysate of step d),
  (ii) providing a fermentation broth by inoculating the cultivation medium with an oleaginous microbe,
  (iii) incubating said medium inoculated with said oleaginous microbe allowing lipid to accumulate
  (iv) recovering the lipid from said oleaginous microbe.

Before introducing the lignocellulosic material in step a) and subjected it to the alkaline delignification, the lignocellulosic material may optionally be pre-treated to separate or partly separate hemicellulose from the material.

Thus in one embodiment, the lignocellulosic material is subjected to a treatment, wherein hemicellulose is at least partially removed from the lignocellulosic material as an aqueous hemicellulose hydrolysate before step a).

The microbes used by the method for producing microbial lipids are oleaginous microbe. The oleaginous microbes (as described herein) are capable of accumulating intercellular lipids such that the lipids mounts at least 15% (w/w) of the total biomass (per cell dry weight) of the microbe when it is cultivated under suitable conditions. In a preferred embodiment, the oleaginous microbe is capable of accumulating at least 20% (w/w) of the total biomass of the microbe (per cell dry weight). In one embodiment of the present invention, oleaginous microbe used for the production of lipids is selected from a group comprising yeast and filamentous fungi. Preferably, a method for production of microbial lipid is carried out under aerobic condition. Thus, in one embodiment of the present invention, the incubation in step (iii) is conducted as aerobic cultivation, such as described herein.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The term "comprising", "comprise" and "comprises" herein are intended by the applicant to be optionally substituted with the terms "consisting of", "consist of" or "consists of", respectively, in every instance.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The term "comprising", "comprise" and "comprises" herein are intended by the applicant to be optionally substituted with the terms "consisting of", "consist of" or "consists of", respectively, in every instance.

Items

In the following the invention is described by way of non-limiting items

Item 1. Method for fractionation of a lignocellulosic material, the method comprising
 a) Subjecting the lignocellulosic material to a delignification treatment in the presence of an alkaline delignification agent to produce a mixture comprising a first solid phase and a first liquid phase containing dissolved lignin,
 b) Separating the first solid phase from the first liquid phase,
 c) Introducing a cationic compound into the first liquid phase to produce a mixture comprising a second solid phase and a second liquid phase,
 d) Subjecting the first solid phase to an enzymatic hydrolysis treatment in the presence of enzymes capable of hydrolysing the hemicellulose and cellulose fractions of the first solid phase to produce a mixture comprising third liquid phase in the form of an enzymatic hydrolysate and a third solid phase.
 e) Separating the third liquid phase from the third solid phase.

Item 2. The method according to item 1, wherein cationic compound is selected from a group comprising cationic polymers and oligomers such as cationic starch polysaccharides, cationic amylose, cationic amylopectin, cationic dextran, cationic lignin oligomers, cationic lignin polymers, cationic peat, or mixtures thereof.

Item 3. The method according to item 2, wherein the cationic polymers and oligomers have a cationic charge density of 0.5-5 meq/g.

Item 4. The method according to item 1, wherein the cationic compound is an elemental cationic ion selected from the group comprising alkaline earth metals and bivalent and trivalent cations of iron (Fe) or aluminium (Al).

Item 5. The method according to item 4, wherein the cationic ion can be derived from compounds such as AlCl3 aluminum chloride, Ba(C2H3O2)2 barium acetate, Ba(HCO3)2 barium bicarbonate, BaBr2 barium bromide, BaCl2 barium chloride, Ba(HCO2)2 barium formate, (Ba(OH)2 barium hydroxide), Ba(NO3)2 barium nitrate, Ca(C2H3O2)2 calcium acetate, Ca(HCO3)2 calcium bicarbonate, CaBr2 calcium bromide, CaCl2 calcium chloride, Ca(HCO2)2 calcium formate, (Ca(OH)2 calcium hydroxide), Ca(NO3)2 calcium nitrate, Mg(C2H3O2)2 magnesium acetate, Mg(HCO3)2 magnesium bicarbonate, MgBr2 magnesium bromide, MgCl2 magnesium chloride, Mg(HCO2)2 magnesium formate, (Mg(OH)2 magnesium hydroxide), Mg(NO3)2 magnesium nitrate, Fe(C2H3O2)2 iron acetate, FeCl3 ferric chloride, and the corresponding hydrates.

Item 6. The method according to any one of the preceding items, wherein the amount of cationic compound is 0.001-0.25 g/g based on the dry matter content of the first liquid phase.

Item 7. The method according to any one of the preceding items, wherein the second liquid phase is separated from the second solid phase and the second liquid phase is recycled to step a)

Item 8. The method according to any one of the preceding items, wherein the alkaline delignification agent is selected from a group consisting of sodium hydroxide, sodium carbonate, potassium hydroxide, potassium carbonate, calcium hydroxide, and calcium carbonate, lithium hydroxide, lithium carbonate, ammonium hydroxide, ammonia, sodium sulphide, and the corresponding hydrates.

Item 9. The method according to any one of the preceding items, wherein the concentration of delignification agent is from 0.1 to 10 wt %-, more preferably 0.1-4 wt-% based on the amount of lignocellulosic material on dry matter basis Item 10. The method according to any one of the preceding items, wherein the alkaline delignification agent is added to the lignocellulosic material to obtain a suspension having a pH of above 7, preferably between 10 and 13.

Item 11. The method according to any one of the preceding items, wherein the delignification treatment is conducted at a temperature of above 25° C., preferably between 30 and 160° C.

Item 12. The method according to any one of the preceding items, wherein the lignocellulosic material is subjected to a treatment wherein hemicellulose is at least partially removed from the lignocellulosic material as an aqueous hemicellulose hydrolysate, before the lignocellulosic material is subjected to step a).

Item 13. The method according to item 12, wherein the hemicellulose is at least partly removed from the lignocellulosic material by hydrothermal treatment.

Item 14: The method according to item 12, wherein the hemicellulose is at least partly removed from the lignocellulosic material by autohydrolysis treatment.

Item 15. The method according to item 12, wherein the lignocellulosic material, from which at least part of the hemicellulose is removed, is subjected to a steam explosion before step a)

Item 16. The method according to item 12, wherein at least part of the aqueous hemicellulosic hydrolysate is enzymatically hydrolysed, optionally by combining hemicellulosic hydrolysate with the first solid phase before subjecting the mixture to enzymatic hydrolysis treatment.

Item 17. The method according to any one of the preceding items, wherein the enzymatic hydrolysis is conducted as a batch hydrolysis.

Item 18. The method according to any one of the preceding items, wherein the enzymatic hydrolysis is conducted as a sequential hydrolysis.

Item 19. The method according to any of one of the preceding items, wherein the enzymatic hydrolysis is conducted as a solids-recycle hydrolysis.

Item 20. The method according to any of one of the preceding items further comprising a step of concentrating the third liquid phase.

Item 21. A liquid phase in the form of an enzymatic hydrolysate obtainable by the method according to any one of the preceding items.

Item 22. A concentrated sugar hydrolysate obtainable by the method according to item 20.

Item 23. A method for production of microbial lipid, the method comprising (i) providing a cultivation medium comprising the a third liquid phase in the form of an enzymatic hydrolysate of item 21 or concentrated sugar hydrolysate according to item 22,
(ii) providing a fermentation broth by inoculating the cultivation medium with an oleaginous microbe,
(iii) incubating said medium inoculated with said oleaginous microbe allowing lipid to accumulate,
(iv) recovering the lipid from said oleaginous microbe.

Item 24. The method for production of microbial lipid according to the preceding item, the method comprising
a) Subjecting the lignocellulosic material to a delignification treatment in the presence of an alkaline delignification agent to produce a mixture comprising a first solid phase and a first liquid phase containing dissolved lignin,
b) Separating the first solid phase from the first liquid phase,
c) Introducing a cationic compound into the first liquid phase to produce a mixture comprising a second solid phase and a second liquid phase,
d) Subjecting the first solid phase to an enzymatic hydrolysis treatment to hydrolyse the hemicellulose and cellulose fractions of the first solid phase to produce a mixture comprising a third liquid phase and a third solid phase comprising lignin,
e) Separating the third liquid phase from the third solid phase,
(i) providing a cultivation medium comprising the third liquid phase in the form of an enzymatic hydrolysate of step e),
(ii) providing a fermentation broth by inoculating the cultivation medium with an oleaginous microbe,
(iii) incubating said medium inoculated with said oleaginous microbe allowing lipid to accumulate
(iv) recovering the lipid from said oleaginous microbe.

Item 25. The method according to item 23 or 24, wherein the microbe is selected from the group consisting of yeast and filamentous fungi.

Item 26. The method according to any one of items 23-25, wherein the lignocellulosic material is subjected to a treatment, wherein hemicellulose is at least partially removed from the lignocellulosic material as an aqueous hemicellulose hydrolysate before step a).

Item 27. The method according to any one of the preceding items, wherein at least part of the aqueous hemicellulosic hydrolysate is combined with the first solid phase and subjected to the enzymatic hydrolysis treatment.

Item 28. The method according to any one of items 23-25, wherein the cultivation medium comprises at least part of the first liquid phase.

EXAMPLES

The invention is illustrated by the following non-limiting examples. The invention can be applied to other lignocellulosic raw materials than those illustrated in examples. It should be understood that the embodiments given in the description above and in the examples are for illustrative purposes only, and that various changes and modifications are possible within the scope of invention.

Example 1

Autohydrolysis (with Pre-Adjusted pH) of Wheat Straw
A suspension was prepared by mixing 20 g wheat straw previously milled to pass a 1 mm screen and 180 g water. The suspension was adjusted with acetic acid to pH 4.5. The suspension was transferred into an autoclave reactor that was then non-isothermally heated up with a heating jacket to temperature between 170° C. and 200° C. with continuous stirring. The temperature data during the heating was recorded and used to calculate autohydrolysis severity (Eq. 1). The reactor was cooled to approximately 50 C, and the suspension was manually recovered for filtration. The liquid fraction was separated from the solid fraction and furfural and hydroxymethyl furfural (HMF) in the liquid fraction were measured using HPLC. Total concentration of sugar (g/l) in the liquid fraction was determined after dilute acid hydrolysis that converts oligomeric and polymeric sugars into monosaccharides. The solid fraction was washed with water (0.5 dm3) and pressed. The obtained solid residue was weighed, sampled for dry matter determination, and the yield of solid residue (%) was calculated as the weight ratio of solid residue to the wheat straw weighed to the autohydrolysis treatment (100%*g dry wheat straw/g dry solid residue). Soluble phenolic substances in the liquid were determined using the Folin-Ciocalteu method with guiaiacol as standard.

Figure 15:
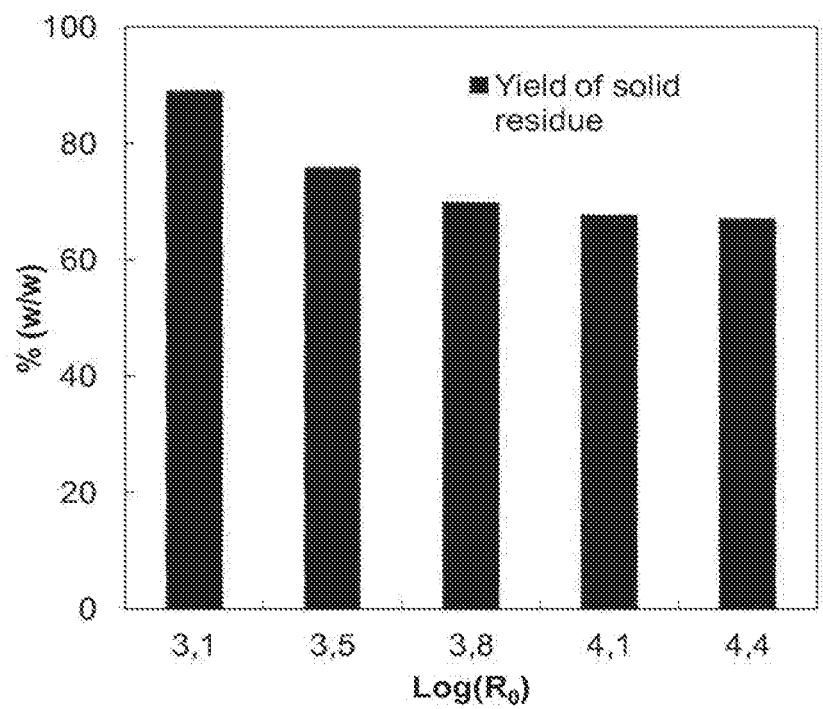
FIG. 15 presents yield of solid residue from autohydrolysis of wheat straw.
Figure 16:
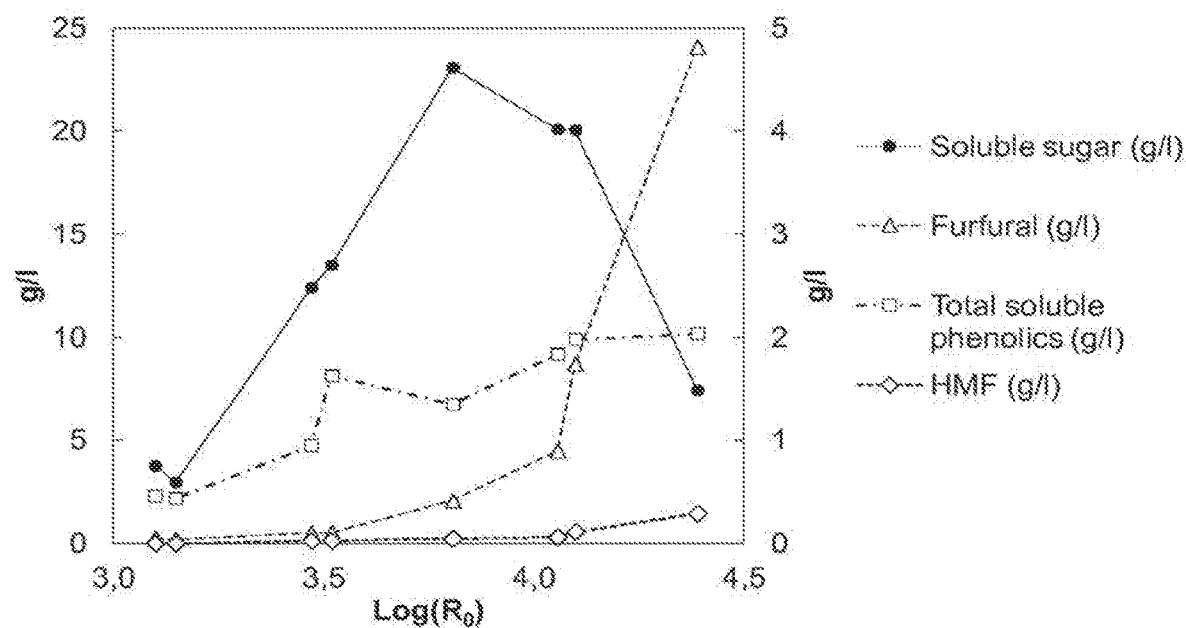
FIG. 16 presents the concentration of total soluble sugar (g/l, left y-axis) and potential microbial inhibitor substances; furfural, hydroxymethyl furfural (HMF) and soluble phenolics (g/l, right y-axis) in the liquid fraction obtained from autohydrolysis of wheat straw at 10% consistency (g straw solids dry matter/g total).

The results shown in FIG. 15 and FIG. 16 summarize the results. The yield of solid residue decreased with autohydrolysis severity with 67% yield at the highest severity (Log(R0)=4.4) (FIG. 15). The concentration of monosaccharide sugars in the liquid fraction first increased and then decreased with increasing autohydrolysis severity. The maximum concentration of sugar (23.1 g/l) was obtained when autohydrolysis severity was Log(R0)=3.8. Beyond this autohydrolysis severity the concentration of sugar in the liquid fraction drastically decreased and concentration of furfural and HMF suddenly increased reaching concentration of 4.8 g/l and 0.3 g/l, respectively. In contrast to the sudden generation of furfural and HMF, the concentration of soluble phenolics increased progressively from 0.5 g/l up to 2.0 g/l with increasing autohydrolysis severity.

This example shows that optimal autohydrolysis conditions in terms of autohydrolysis severity (Log(R0)) can be selected to avoid excess formation of furfural, HMF, and soluble phenolics while maximizing the concentration of monosaccharides in the liquid fraction.

Example 2

A suspension was prepared by mixing 33.8 kg chopped wheat straw containing 11% moisture with 350 kg of tap water giving consistency of 8.5%. The suspension was heated up to approximately 60° C., and the liquid fraction separated from the solids by filtration in an agitated Nutsche Filter. The solid fraction (31.2 kg dry matter) was mixed with water to give 192.4 kg of suspension at 5% consistency. The suspension was heated to 180° C. and cooled down to room temperature giving severity of S=4.15. The solid fraction was separated from the liquid fraction in a decanter centrifuge. The solid fraction was washed with water, and the washed insoluble fraction "autohydrolyzed straw" (15.3 kg dry matter) was recovered using the decanter centrifuge and stored in freezer. Based on HPLC analysis, the liquid fraction (6.3 kg dry matter) contained hemicellulose-derived sugars approximately half of its dry matter.

Separation of the liquid and solid fraction and optional washing of the solid fraction separates soluble phenolic substances and organic acids released in autohydrolysis from the autohydrolyzed solid fraction. As a result, consumption of alkaline delignification chemical in the subsequent delignification step is synergistically decreased.

The example shows that autohydrolysis enables separation of hemicellulosic sugars from lignocellulosic material before further hydrolysis treatments. The solid fraction produced from this experiment was used subsequently in the delignification tests, which resulted in solid fraction with low lignin and high carbohydrate content.

Example 3

A suspension was prepared by mixing 10.5 kg of milled straw at 7.3% moisture and 54.1 kg of tap water in a 100 dm3 container. After storing at room temperature for 18 h, 64.2 kg of the suspension was weighed into a horizontal cylindrical 250 dm3 stirred autoclave reactor. The reactor was closed and heated within 75 min to 140° C., maintained at 140° C. for 5 h and cooled to room temperature within 30 min. The hydrothermally treated suspension was removed from the reactor, and liquid and solid fractions were separated by filtration. The solid fraction was washed with tap water and pressed using a hydro-press. The pressed solid fraction (20.9 kg) had 42.7% dry matter content.

The solid fraction produced from this experiment was used subsequently in the delignification tests, which resulted in solid fraction with low lignin and high carbohydrate content.

Delignification of Autohydrolyzed Straw

Autohydrolysed straw contains considerable amounts of lignin that causes inhibitory effects in the enzymatic hydrolysis. For this reason the solid material from auto hydrolysis is extracted in alkaline conditions to remove lignin prior to enzymatic hydrolysis.

Example 4

A suspension was prepared by mixing 20.5 kg (8 kg dry matter) of autohydrolysed straw from the Example 2 with 262 g granular NaOH and tap water in a 180 dm3 stainless steel reactor equipped with a stirring unit. The suspension at 6.6% consistency was treated by heating the reactor to 95° C. in in 30 min followed by isothermal treatment at 95° C. for 1 h with continuous stirring. The extracted solid fraction was separated from the liquid fraction by filtration in a centrifuge, washed with tap water, pressed and the NaOH-extracted AH-straw (23.64 kg, 27% dry matter content) was stored in 6° C. The liquid fraction ("NaOH delignification solution") containing 1.62 kg dissolved material from autohydrolysed straw was stored at 6° C.

Enzymatic hydrolysis of the NaOH-extracted AH-straw with an enzyme dose of 35 µl/g Flashzyme Plus (Roal Oy, Finland), which was equal to 6 FPU (filter paper unit)/g DM of cellulase activity, gave 65.0% sugar yield from autohydrolysed straw carbohydrates. This is an improved result compared to 61.0% sugar yield from autohydrolysed straw carbohydrates without delignification.

The sugar yield is calculated as the ratio of total amount of monosaccharides released in enzymatic hydrolysis of NaOH-extracted AH-straw to total amount of mosaccharides released from similar weight of AH-straw in acid hydrolysis multiplied with the dry matter yield of NaOH-extracted AH-straw from the delignification treatment This example shows that the same enzyme amount produces higher yield of sugar in enzymatic hydrolysis, when lignin is removed before the enzymatic hydrolysis by alkaline treatment (NaOH). The example also shows that part of the lignin is dissolved in alkaline liquid fraction and that the lignin can be recovered by precipitation.

Example 5

A suspension at 3.6% consistency was prepared by mixing autohydrolysed straw from the Example 2 (403 g, 156 g dry matter) with 4050 g tap water and 37.5 g solid $Na_2CO_3$ in a glass reactor equipped with a magnetic stirrer. The reactor was heated up to 95-100° C. in 30 min and treated for 4 h at 95-100° C. with continuous stirring of the suspension. 812 g of Na2CO3-extracted solid fraction ("Na2CO3-extracted AH-straw") having a 15% dry matter content was separated from the liquid fraction (3325 g) by filtration, washed with tap water, pressed and stored in 6° C. The yield of the solid fraction (DM of delignified straw/DM of autohydrolysed straw) was 78%. The liquid fraction (Na2CO3 delignification solution) had pH 9.8 and was stored at 6° C. The amount of used carbonate is higher that NaOH since the carbonate is a weaker base than the hydroxide.

Enzymatic hydrolysis of Na2CO3-extracted AH-straw with an enzyme dose of 35 µl/g Flashzyme Plus (Roal Oy, Finland), which was equal to 6 FPU (filter paper unit)/g DM of cellulase activity, gave 59.1% sugar yield from autohydrolysed straw carbohydrates. This was less than 65.0% sugar yield with NaOH-extracted AH-straw from autohydrolysed straw carbohydrates or 61.0% sugar yield from autohydrolyzed straw carbohydrates without delignification.

The sugar yield is calculated as the ratio of total amount of monosaccharides released in enzymatic hydrolysis to total amount of mosaccharides released from similar weight of AH-straw in acid hydrolysis multiplied with the dry matter yield of Na2CO3-extracted AH-straw from the delignification treatment.

Compared to autohydrolysed straw that was subjected to enzymatic hydrolysis without delignification, advantage of the Na2CO3-delignification was that additional lignin fraction (Na2CO3 delignification solution) was obtained.

This example shows that the same enzyme amount produces higher yield of sugar in enzymatic hydrolysis, when lignin is removed before the enzymatic hydrolysis by alkaline treatment ($Na_2CO_3$). The example also shows that part of the lignin is dissolved in alkaline liquid fraction and that the lignin can be recovered by precipitation

Example 6

A suspension was prepared by mixing 10.0 kg (4.41 kg dry matter) of autohydrolysed straw from the Example 3 with tap water (29.5 kg) and 3.401 g of 50% (w/w) aqueous NaOH. The suspension was treated in similar reactor and thermal conditions as described above in Example 3. The solid fraction ("NaOH-delignified straw"), was separated by filtration, and after washing had 30.4% dry matter content. The liquid fraction ("NaOH delignification solution") had pH 13.0 and was stored in 6° C.

Example 7

The purpose of the example was to study the effect of alkaline treatment of autohydrolysed straw on enzymatic hydrolysis and sugar yield from autohydrolysed straw. To achieve this, a suspension at 7.5% consistency was prepared by mixing 15 g of dry matter of autohydrolysed straw from Example 1 with deionized water and chemicals listed in Table 1. The different alkaline chemicals were used to adjust pH before the heating to the indicated value. The suspension was heated rapidly to 90° C. in a microwave oven. The hot suspension was filtered to separate solid and liquid fractions. The solid fraction was washed with water and the filter cake stirred to homogeneity, and its dry matter content was measured. The washed solid fraction (10 g of dry matter) was hydrolysed with 350 µL (6 FPU/g) of cellulolytic preparation Flashzyme Plus (Roal, Finland) at 10% consistency in 0.05 M Na-acetate buffer at pH 5 in presence of potassium sorbate. Hydrolysis was carried out in 250 mL conical flask placed in a thermostatic incubator set at 50° C. reaction continued with 200 rpm shaking for 72 h. Released monomeric sugars were determined from the liquid fraction by HPLC. The obtained dry matter and sugar yields are presented in Table 1.

The example shows that delignification of autohydrolysed straw increases the sugar yield from the autohydrolysed straw by enzymatic hydrolysis even when dry matter losses in delignification treatment are taken into account. Another advantage of the delignification treatment is generation of soluble lignin fraction suitable for further processing.

Surprising finding of the example was that only a low amount of alkaline chemical is needed in delignification of autohydrolysed straw. Another surprising finding was that pH of the liquid fraction isolated from the delignified solid fraction was relatively low which means that lower amount of acid is needed to precipitate lignin from the solution by decreasing the pH.

Example 8

The purpose of the example was to study the effect of cationic starch on precipitation of lignin from delignification liquor where alkalinity is caused by NaOH. In the experiment, 15 g of pH 10 NaOH lignin solution from Example 6 (1.5% dry matter content) was weighed into a glass test tube. A precise weight of cationic starch "Raifix 25035" (Chemigate, Finland) was added to the test tube. The tube containing the mixture was covered by rubber cork, shaken to mix the ingredients, and let stand at room temperature. Depending on the amount of added cationic starch, but usually after a few minutes, phase separation in the mixture was observed. After 4 h, 0.1 mL sample was withdrawn from the upper phase of the mixture diluted 1:10 in alkaline water, centrifuged 5 min at 10000 g, and absorbance at 280 nm and 600 nm was measured from the supernatant with appropriate dilutions in alkaline water. Compared to the absorbance of the untreated lignin solution, percentage decrease in absorbance at 280 nm or 600 nm was calculated. The decrease in absorbance from the supernatant indicates the lignin removal (precipitation) from the liquid by the cationic compound (cationic starch).

The results in FIG. 5 show the effect of cationic starch dosage on percentage decrease in UV 280 nm absorbance or dissolved matter. Absorbance was clearly decreased the most when dosage of cationic starch was between 0.2 g/g to 0.6 g/g with the amounts given on dry matter basis. After 24 h incubation, the liquid phase was decanted off and passed through grade 1 porosity glass sinter filter. The filtrate was collected, and tested for pH showing values between pH 9.4 and pH 9.6 and for the untreated solution pH 9.5. Cationic starch dosage could not be attributed to change in pH but, instead, the decrease from the initial pH 10 was likely due to absorption of carbon dioxide from air. Both gravimetric and spectrophotometric analysis gave similar result with respect to the observed maximum precipitation.

The results indicate that cationic compound, such as cationic starch, can be used to precipitate lignin from alkaline delignification liquid where alkalinity is caused by hydroxide compound, such as NaOH, without adjustment of pH.

Example 9

Figure 6:
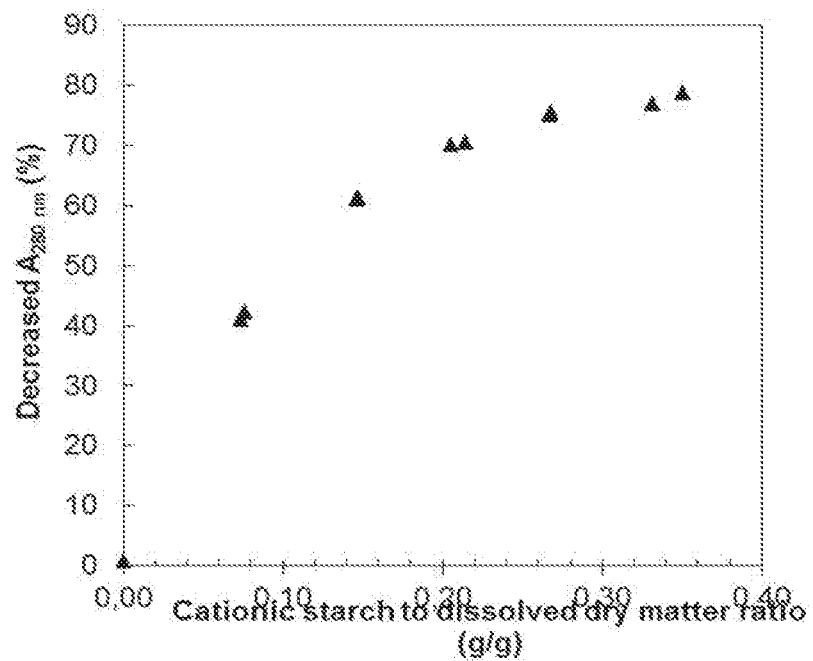
FIG. 6 presents the effect of cationic starch dosage on percentage decrease in absorbance at 280 nm and 600 nm after 4 h incubation of Na2CO3 delignification solution at room temperature.

The purpose of the example was to study the effect of cationic starch on precipitation of lignin from delignification liquor where alkalinity is caused by $Na_2CO_3$ instead of NaOH. $Na_2CO_3$ delignification solution at pH 9.8 from Example 5 was treated with the cationic starch "Raifix 25035" as described above, but with lower dosage of the cationic starch. Decrease in absorbance at 280 nm after 4 h incubation was measured relative to the absorbance measured from the untreated lignin solution. Results presented in FIG. 6 show increasing trend between the dosage of cationic starch and decrease in absorbance at 280 nm. Up to 79% decrease in absorbance at 280 nm was obtained when the dosage of cationic starch to dry matter of the lignin solution was 0.35 g/g.

Figure 7:
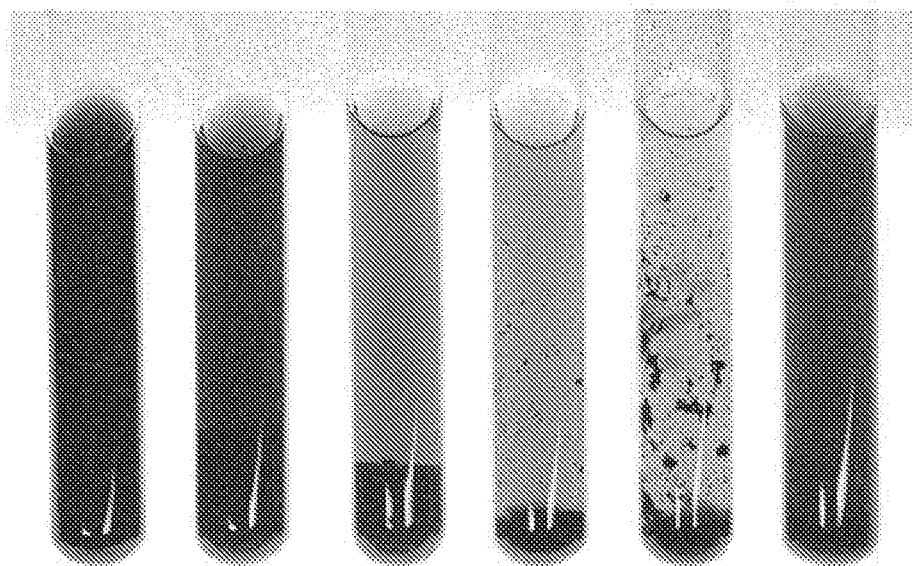
FIG. 7 presents a photograph of the test tubes containing $Na_2CO_3$ delignification solution 8 h after supplementation of cationic starch "Raifix 25035". The dosage of cationic starch to dry matter of the delignification solutions was from left to right 0 mg/g, 0.074 g/g, 0.147 g/g, 0.214 g/g, 0.267 g/g, and 0.332 g/g.

To illustrate the effect of cationic starch on precipitation of delignification solutions, in FIG. 7 a photograph of the tubes taken after 8 h reaction time is shown. In contrast to slight decrease of alkalinity in Example 8 after 24 h reaction, no change in pH was observed in the current example.

Visual observation of the tubes shown in FIG. 7 confirmed the quantitative results of the precipitation of lignin. It is clear from the results shown in FIG. 5 and FIG. 6 that the cationic starch "Raifix 25035" precipitated up to 80% of ultraviolet light absorbing material from the delignification solutions.

The results indicate that cationic compound, such as cationic starch, can be used to precipitate lignin from alkaline delignification liquid where alkalinity is caused by carbonate compound, such as Na2CO3, without adjustment of pH.

Example 10

Figure 8:
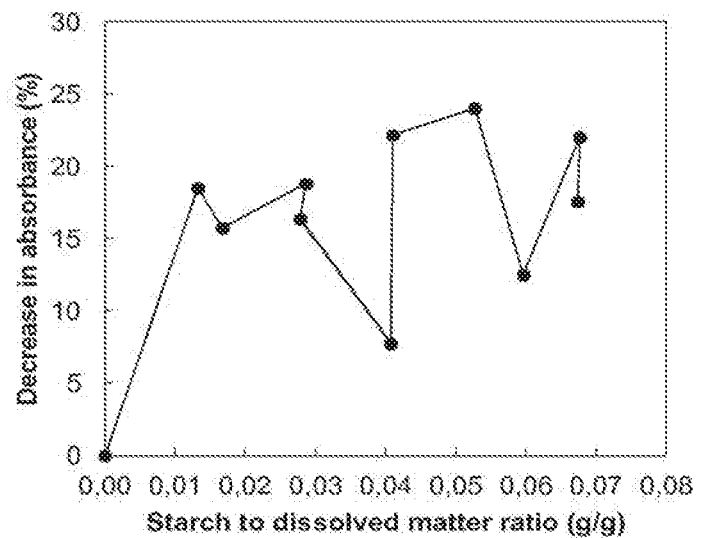
FIG. 8 presents the effect of dosage of cationic starch "Raifix 25035" on decrease in absorbance at 280 nm.
Figure 9:
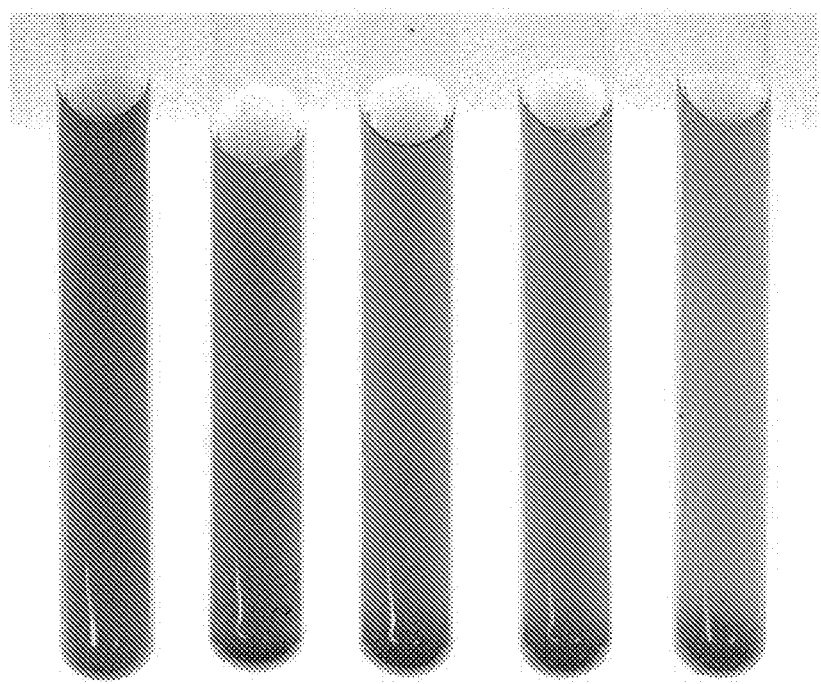
FIG. 9 shows a photograph of the test tubes containing non-alkaline liquid 24 h after supplementation of cationic starch "Raifix 25035". The dosage of cationic starch to dry matter of the non-alkaline liquid was from left to right 0 mg/g, 13 mg/g, 28 mg/g, 41 mg/g, and 68 mg/g.

The purpose of the example was to study the effect of alkalinity on precipitation of lignin by cationic starch. A non-alkaline solution was obtained by acidification of the NaOH delignification solution from Example 6 by 6 M sulfuric acid to pH 5. The liquid fraction ("non-alkaline liquid") was separated from the precipitated solids by centrifugation and filtration. 15 g of the liquid (6.3% dry matter content) was treated with the cationic starch "Raifix 25035" as described above in Example 9, but at different dosage of the cationic starch. Decrease in absorbance at 280 nm after 4 h incubation was measured relative to the absorbance measured from the untreated lignin solution. Results presented in FIG. 8 show that decrease in absorbance at 280 nm was between 8% and 24% when the ratio of cationic starch dosage to the total dissolved matter was between 0.01 g/g and 0.07 g/g. It is worth to note that the non-alkaline liquid at pH 5 contained large proportion of its dissolved matter as sulfate salts. To further illustrate the effect of cationic starch on the non-alkaline liquid, in FIG. 9 a photograph of the tubes taken after 24 h reaction time is shown.

As indicated in FIG. 8, a low degree of precipitation was obtained from the non-alkaline liquid at pH 5 when supplemented with cationic starch "Raifix 25035". Thus the present invention results in more efficient precipitation of lignin from alkaline solutions compared to precipitation of lignin from non-alkaline solutions.

Example 11

A suspension was prepared by mixing 100 kg of pre-cleaned wheat straw containing 7% moisture with 374 kg of alkaline delignification recycle solution having 6.4% dry matter content and a pH of 12.8. The suspension was subjected to delignification treatment at a temperature of 70° C. and pH of 12 for 2 hours. The extracted solid fraction was separated from the liquid fraction by pressure filtration, washed with water. The NaOH-extracted straw had a dry matter content of 35% and it contained mostly cellulose and xylan.

The liquid fraction (NaOH delignification solution) was treated with 1.2 kg of cationic starch (Raifix 01035) having 40% dry matter content to obtain a solid precipitate containing lignin and an alkaline liquid fraction. The precipitate was separated from the alkaline liquid phase by settling and centrifuging and the alkaline liquid was recycled to the delignification treatment.

This example shows that lignin can be effectively separated from pre-treated lignocellulosic material and that dissolved lignin can be recovered from NaOH delignification solution by flocculating with an cationic compound The example indicates that the alkaline delignification liqueur can be recycled after precipitation of lignin by cationic compound and the removal of the precipitate.

Example 12

Precipitation of Lignin Dissolved in Alkaline Solutions

Wheat straw was grinded with a hammer mill and a 2.445 kg portion was immersed in 46.615 kg water to form a total mass of 49.060 kg. This mixture was made alkaline by 771 gram of 50% NaOH solution. The suspension was heated in 200-L mixing chamber for 4 h at 60° C. with 100 rpm mixing. Thereafter the suspension was filtered at the same temperature. The alkaline supernatant, having dry matter content of 2.8% was taken for subsequent treatment.

The supernatant was supplemented with cationic starch (Raifix 25035) to 5% (w/w) concentration. The precipitation formed was separated and thereafter the dry weight concentration of the supernatant was 2.5%.

In another experiment the supernatant having dry matter content of 2.8% was supplemented with either Ca-acetate or CaCl2 to Ca2+ concentration of 2% as calculated per dry weight of the supernatant. After separation of the precipitate the dry matter content of determined as shown in Tables 2 and 3.

Still in another set of experiments the alkaline supernatant with initial dry matter content of 2.8% was first treated with the cationic starch as described above and after removal of the precipitate the supernatant was treated with the calcium salts as also described above. The results are shown in Tables 2 and 3.

TABLE 2

Precipitation of lignin from alkaline supernatant by Ca-acetate and by consecutive treatments, first with cationic starch and then with Ca-acetate.

| Sample | Dry matter in supernatant, % | Added Ca$^{2+}$, % from dry matter of supernatant | Dry matter of supernatant after removal of precipitate, % |
|---|---|---|---|
| Alkaline lignin supernatant | 2.73% | 2.9% | 3.1% |
| Alkaline lignin supernatant | 2.73% | 5.8% | 2.65% |
| Alkaline lignin supernatant after cationic starch treatment | 2.84% | 5.6% | 2.73% |

TABLE 3

Precipitation of lignin from alkaline supernatant by Ca-acetate and by consecutive treatments, first with cationic starch and then with Ca-acetate.

| Sample | Dry matter in supernatant, % | Added Ca$^{2+}$, % from dry matter of supernatant | Dry matter of supernatant after removal of precipitate, % |
|---|---|---|---|
| Alkaline lignin supernatant | 2.73 | 2.4 | 2.77 |
| Alkaline lignin supernatant after cationic starch treatment | 2.84 | 2.5 | 2.45 |

The example shows that lignin can be removed from alkaline solutions by precipitation enabling the use of delignified supernatant as a source of alkali in the treatment of lignocellulose.

Examples on Enzymatic Hydrolysis of Autohydrolyzed and/or Delignified Straw

Example 13

A comparison of NaOH-delignified straw (material from the Example 6) and autohydrolysed straw (material from the Example 1) was performed in three different enzyme hydrolysis processes, including batch hydrolysis, sequential hydrolysis and solids-recycling at a constant process feed. An enzyme mixture was used, comprising 85% cellulase (Econase CE, Roal Oy), 10% cellobiase (Novozyme 188, Sigma/Novozymes) and 5% xylanase (GC140, Genencor). Reactions were performed at pH 5 and at temperature of 50° C. in a shaker at 200 rpm.

Batch Hydrolysis

Figure 10:
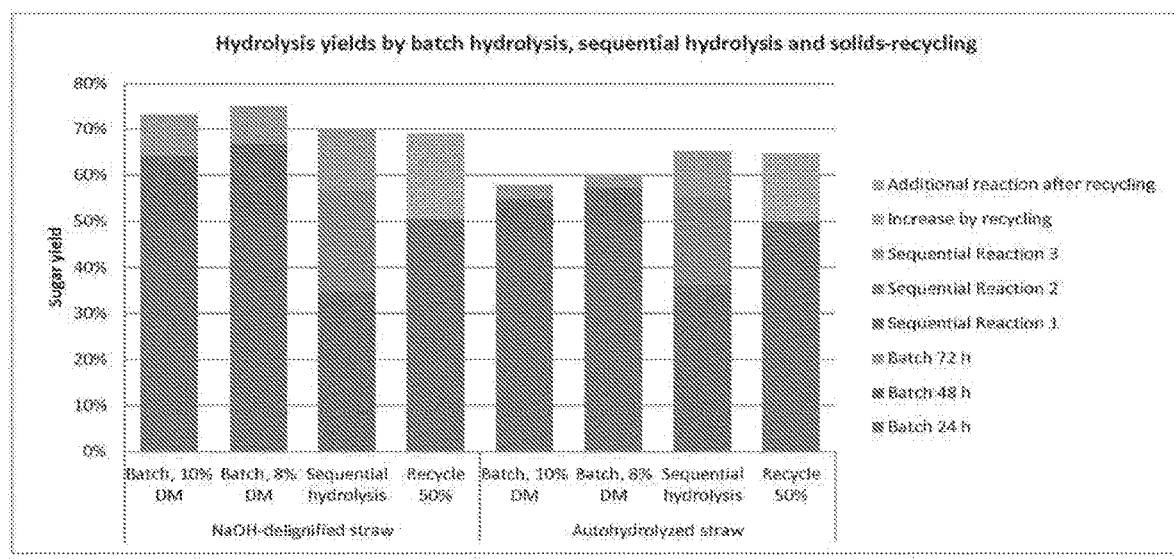
FIG. 10 presents total sugar yields from NaOH-delignified straw and autohydrolysed straw in batch hydrolysis after 24 h, 48 h and 72 h, after the 1st, 2nd and and 3rd sequential hydrolysis and after solids recycling and an additional 24 h reaction.

A batch hydrolysis was performed to NaOH-delignified straw and autohydrolysed straw at 10% consistency and at 8% consistency (where "consistency" was the proportion of insoluble solids in the reaction slurry, w/w). An enzyme dose was used that contained an enzyme activity of 9 FPU/g pre-treated straw DM. The sugar yields (the released anhydrous sugars as percentage of the total polymeric carbohydrates in the material), are shown in FIG. 10. After 24 h, 48 h and 72 h of hydrolysis, the sugar yields from NaOH-delignified straw at 8% and 10% consistency averaged 50%, 65% and 74%, whereas with autohydrolysed straw, the yields at 8% and 10% consistency averaged 49%, 56% and 59%, respectively, showing that a higher sugar yield can be obtained from NaOH-delignified straw with the same enzyme amount than from autohydrolyzed straw. The yields were generally slightly higher at the lower consistency.

Figure 12:
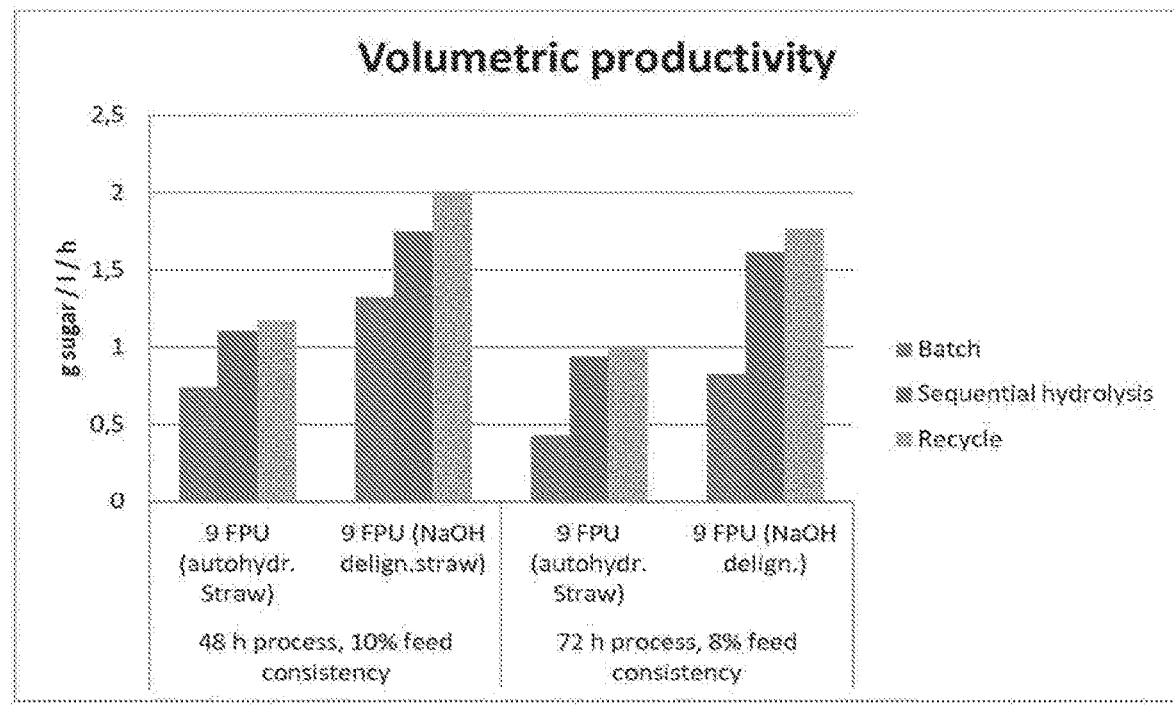
FIG. 12 presents the volumetric sugar productivities of of NaOH-delignified straw and autohydrolysed straw in batch hydrolysis, sequential hydrolysis and solids-recycling. The 48 h process comprises a 48 h batch hydrolysis or two 24 h sequential hydrolysis reactions or a 24 h solids-recycling reaction at steady state with 50% recycle rate. The 72 h process comprises a 72 h batch hydrolysis or three sequential 24 h hydrolyses or the recycling reaction and an additional 24 h hydrolysis.

The volumetric productivity shown in FIG. 12 of the 48 h and 72 h batch hydrolysis of NaOH-deliginified straw was 1.32 g/l/h (grams of sugar per liter of the reaction slurry per hour) and 0.82 g/l/h, respectively, which were considerably higher compared the volumetric productivities of 0.74 g/l/h and 0.42 g/l/h, respectively, obtained from autohydrolysed straw.

Figure 11:
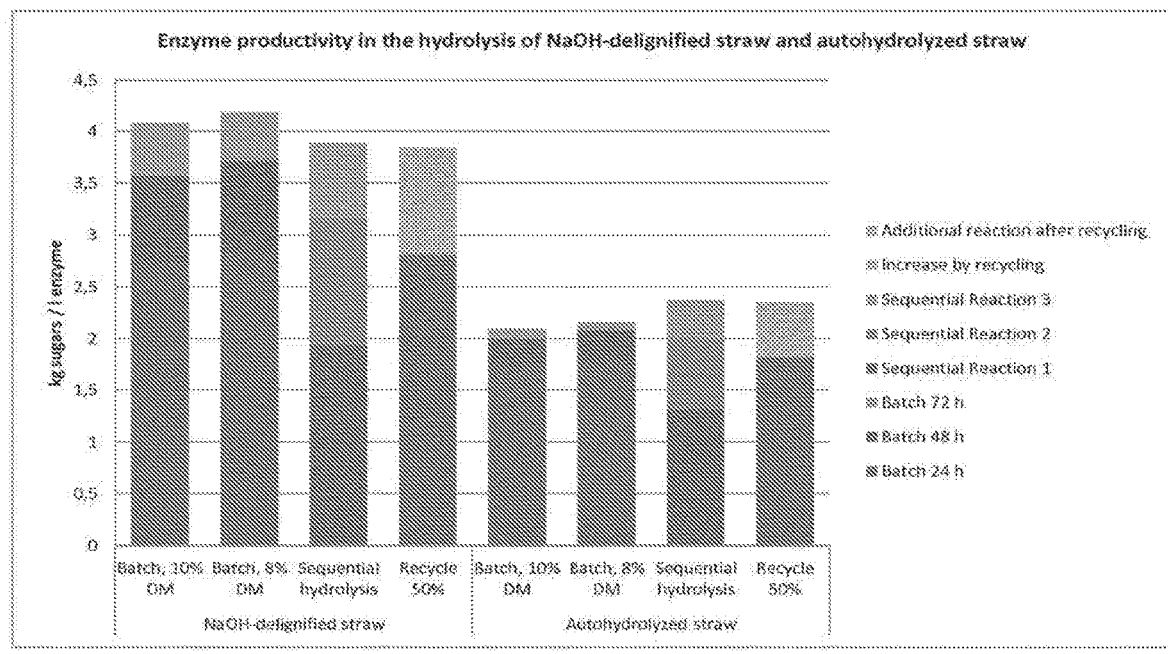
FIG. 11 presents enzyme productivities in the hydrolysis of NaOH-delignified straw and autohydrolysed straw in batch hydrolysis, sequential hydrolysis and solids recycling.

The enzyme productivity (kg sugar obtained with a liter of enzyme) of the reactions is shown in FIG. 11. The enzyme productivity in the 72 h batch hydrolysis of NaOH-delignified straw was 4.2 kg/l enzyme which was almost double compared to the 2.2 kg/l enzyme productivity with autohydrolysed straw.

This example indicates that a higher sugar yield, enzyme productivity and volumetric productivity was obtained from delignified straw compared to autohydrolysed straw in a batchwise enzymatic hydrolysis.

Sequential Hydrolysis

NaOH-delignified straw and autohyrolysed straw were hydrolysed by a three-step hydrolysis that consisted of three sequential 24 h reactions. Between the reactions, liquid was separated from the solids and the solid residue was mixed with fresh liquid and enzymes. The proportion of solids in the total process ("the total consistency" or "the feed consistency") was 10% in the first two reactions and 8% in the three reactions. Because the total liquid amount liquid was divided between the reactions, the actual consistency of the first, second and third reaction were 14.3%, 12.5% and 10.6% with NaOH-delignified straw and 14.4%, 12.9% and 12.8% with autohydrolysed straw, respectively. Similar enzyme cocktail and dose were used, as described in "batch hydrolysis of NaOH-delignified straw." Two thirds (66.6%) of the total enzyme dose was applied in the first reaction and one third (33.3%) in the second reaction.

The sugar yield (the released anhydrous sugars as percentage of the total polymeric carbohydrates in the material, FIG. 10) after the first, the second and the third reaction was 35%, 57% and 70%, respectively, from NaOH-delignified straw and 36%, 55% and 65%, respectively, from autohydrolysed straw. Although the yield was slightly higher from autohydrolysed straw after the first reaction, the yield from NaOH-delignified straw clearly prevailed after the second and third reactions. The total volumetric productivity (FIG. 12) after two and three sequential 24 h reactions was 1.74 g/l/h and 1.61 g/l/h, respectively, with NaOH-delignified straw, which was considerably higher compared to the productivities of 1.10 g/l/h and 0.94 g/l/h, respectively, from autohydrolysed straw. The enzyme productivity after three 24 h reactions with NaOH-delignified straw was 4.4 kg/l enzyme, which was drastically higher compared to the enzyme productivity of 2.4 kg/l with autohydrolysed straw (FIG. 11).

This example indicates that a higher sugar yield, enzyme productivity and volumetric productivity was obtained from delignified straw compared to autohydrolysed straw in a sequential enzymatic hydrolysis.

Hydrolysis with Solids-Recycling

NaOH-delignified straw and autohydrolysed straw were hydrolysed in a solids-recycling process. Multiple subsequent reactions were performed, where fresh pre-treated straw, enzyme and liquid were mixed at 10% consistency. Into the mixture of fresh reaction constituents, 50% of the separated solid residue from the previous reaction was mixed. The recycling of the solid residue led to an increase in the actual reaction consistency, which was increased to 12.3% with NaOH-delignified straw and to 13.2% with autohydrolysed straw. Six subsequent recycling reactions were performed in order to reach a steady state, where the reaction volume, consistency and hydrolysis yield remained constant between subsequent reactions. When steady state was reached, the part of the solid residue that was not recycled was mixed with a constant amount of fresh liquid and an additional 24 h reaction was performed, at a consistency of 10.5% with NaOH-delignified straw and 13.1% with autohydrolysed straw. The total proportion of solids (or "the total consistency" or "the feed consistency") was 10% in the recycling reaction alone and 8% in the process including the recycle reaction and the additional reaction.

The sugar yield as released anhydrous sugars as percentage of the total polymeric carbohydrates in the material, FIG. 10.) in the initial reaction that did not contain any recycled material was 51% and 50% for NaOH-delignified straw and autohydrolysed straw, respectively. After six subsequent reactions with 50% recycling of the solid residue, the hydrolysis yield was increased to 57% and 55% with NaOH-delignified straw and autohydrolysed straw, respectively. After the additional reaction the total sugar yield was 69% and 65% with NaOH-delignified straw and autohydrolysed straw, respectively, thus showing generally higher yields for NaOH-delignified straw. The volumetric productivity of the recycle reaction alone with NaOH-delginified straw and autohydrolysed straw was 1.99 g/l/h and 1.17 g/l/h, respectively, and including the additional reaction, 1.77 g/l/h and 0.99 g/l/h, respectively, showing considerably higher volumetric productivities with NaOH-delignified straw. The enzyme productivity of the recycle reaction alone with NaOH-delginified straw and autohydrolysed straw was 3.2 kg/l and 2.0 kg/l, respectively, and when the additional reaction was included, 3.8 kg/l and 2.4 kg/l, respectively, showing drastically higher enzyme productivity for NaOH-delignified straw compared to autohydrolysed straw.

Figure 13:
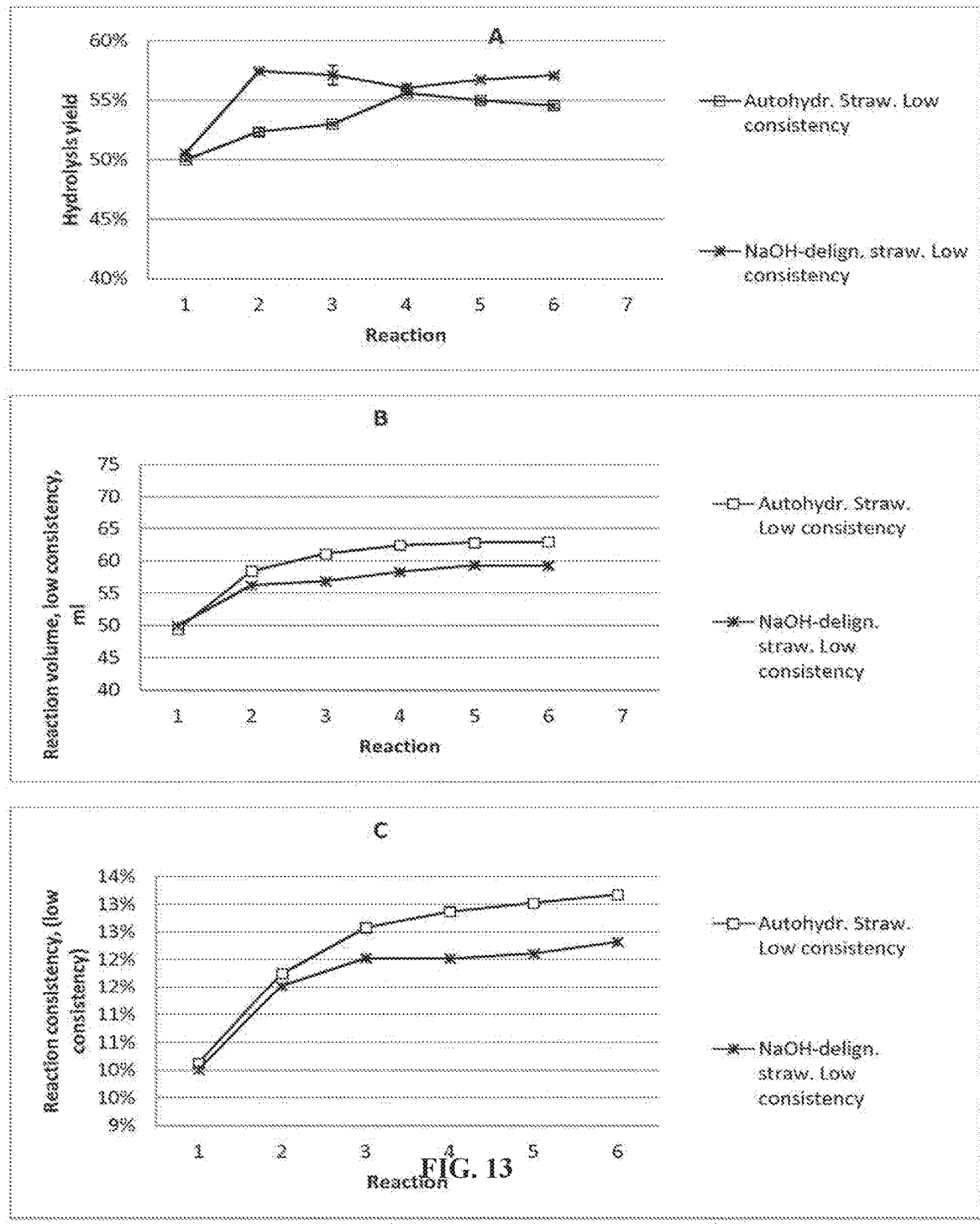
FIG. 13 presents progression (sugar yield, reaction volume and reaction consistency) of consecutive solids-recycling reactions in enzymatic hydrolysis of NaOH-delignified and autohydrolyzed straw with 50% recycle rate in terms of hydrolysis (A), reaction volume (B) and reaction consistency (C).

The progression of the hydrolysis in the subsequent reactions is presented in FIG. 13a. The progression of the reaction volume is presented in FIG. 13b. The progression of the reaction consistency in presented in FIG. 13c.

This example indicates that a higher sugar yield, enzyme productivity and volumetric productivity were obtained from delignified straw compared to autohydrolysed straw in enzymatic hydrolysis process with solids recycling.

Conclusions of Example 13

1. The overall sugar yield was generally higher for NaOH-delignified straw compared to autohydrolysed straw in all different processes.

2. Since the volumetric productivity was higher with NaOH-delginfied straw compared to autohydrolysed straw in all different processes, smaller reactors and separators are required for a given sugar production rate in the hydrolysis of NaOH-delignified straw compared to autohydrolysed straw.

3. Since the enzymatic productivity was higher with NaOH-delignified straw compared to autohydrolysed straw in all different processes, the enzyme cost per kg of obtained sugar is lower with NaOH-delignified straw than with autohydrolysed straw.

4. Equal amounts of water per pre-treated straw were used in this example. It can be concluded that solids-recycling and sequential hydrolysis led to equal hydrolysis yields but increased the volumetric productivities compared to batch hydrolysis.

Example 14

Preparation of Hydrolysates

Autohydrolysis Liquid C

The autohydrolysis reaction for wheat straw and subsequent isolation of hemicellulose oligosaccharides was carried out to produce liquid fraction for fermentation, and solid fraction susceptible for enzymatic hydrolysis. To achieve this, 35.7 kg wheat straw (89.8% dry matter content) was mixed with 240 kg of water giving suspension at 11.6% consistency in a 500 dm3 stirred tank reactor. The suspension was heated up to 180° C. followed by cooling to below 100° C. The hydrothermally treated suspension was discharged from the reactor and the first liquid fraction separated from the solid fraction using a decanter centrifuge. The solid fraction was suspension-washed in acidic water adjusted to pH 4 with phosphoric acid. The solid fraction was separated from the second liquid fraction in the decanter centrifuge. The first and second liquid fractions were combined and concentrated in a falling film evaporator to give 18.3 kg of concentrated autohydrolysis liquid forming autohydrolysis liquid C containing hemicellulose sugars partly in oligomeric from and having 42% dry matter content and 38° Bx refractometric dry substance. The washed solid fraction (96.7 kg having 23.0% dry matter content) was used as feed material for enzymatic hydrolysis to produce cellulose hydrolysate for cultivation.

Part of the phenolic compounds the autohydrolysis liquid concentrate contained were removed by treating the liquid by adding 40 g/l activated carbon, mixing gently for 20 hours in 4 C and finally filtering the carbon away using 400 um filtration cloth.

Enzymatic hydrolysate from cellulose fraction of wheat straw was prepared from the solid fraction containing cellulose (after washing) from autohydrolysis experiment where autohydrolysis liquid C was prepared. The washed solid fraction from autohydrolysis treatment forming autohydrolysis liquid C (17.3 kg having 23.1% dry matter content) was weighed into a 40 dm3 stirred-tank reactor and mixed with 14.7 kg water and 10 mL 50% NaOH (w/w) to give suspension at 12.5% consistency and at pH 5. The reactor was heated up and maintained at 50° C. and 216 ml of enzyme mixture comprising 82% cellulose (Econase CE, Roal Oy), 10% cellobiase (Novozyme 188, Sigma/Novozymes) and 7% xylanase (GC140, Genencor). During the enzymatic treatment the suspension was stirred periodically three times per hour for 5 min. After 48 h residence time the suspension was supplemented with fresh enzyme mixture amounting 10% of the initial enzyme dosage and having similar proportions of individual enzymes. After 72 h residence time at 50° C. the liquid fraction was separated from the solid fraction by filtration using a hydropress. The solid fraction was washed once with water and the liquid fraction again separated from the solid fraction. The liquid fractions were combined and concentrated by evaporation under reduced pressure. The cellulosic hydrolysate concentrate (1.57 kg) contained 220 g/l total sugar.

The cellulose hydrosate containing monomeric sugars was used as such in cultivation.

Single Cell Oil Production

The experiments were done using a lipid producing fungal strain *Aspergillus oryzae*. From the sporulating fungus grown on PDA-plates a spore suspension was made by adding 12 ml of sterile water and the spores were scraped off with inoculation loop to the liquid. 24 ml of the spore suspension was directly used for fermentor inoculation. The medium composition is presented in table 4. Purified autohydrolysis liquid C (hemicellulose solution, hemicellulosic sugars) and the cellulose hydrolysate from the same experiment was used in the cultivation. The cultivation was done in Biostat B plus 5 l fermentor in 3 l volume, and during it the stirring was set to 500 rpm, pH was kept in 5.5 with 3 M NaOH, the aeration was 1 vvm and the temperature 35 C during growth, in lipid production it was lowered to 28 C.

TABLE 4

Composition of growth medium

| Medium components | Concentration (g/l) |
|---|---|
| Hemicellulosic sugars | 20 |
| Yeast extract | 2 |
| (NH4)2SO4 | 1.5 |
| MgCl * 6H2O | 1.5 |
| K2HPO4 | 0.8 |
| KH2PO4 | 1.5 |
| CaCl2 * 2H2O | 0.3 |

Figure 14:
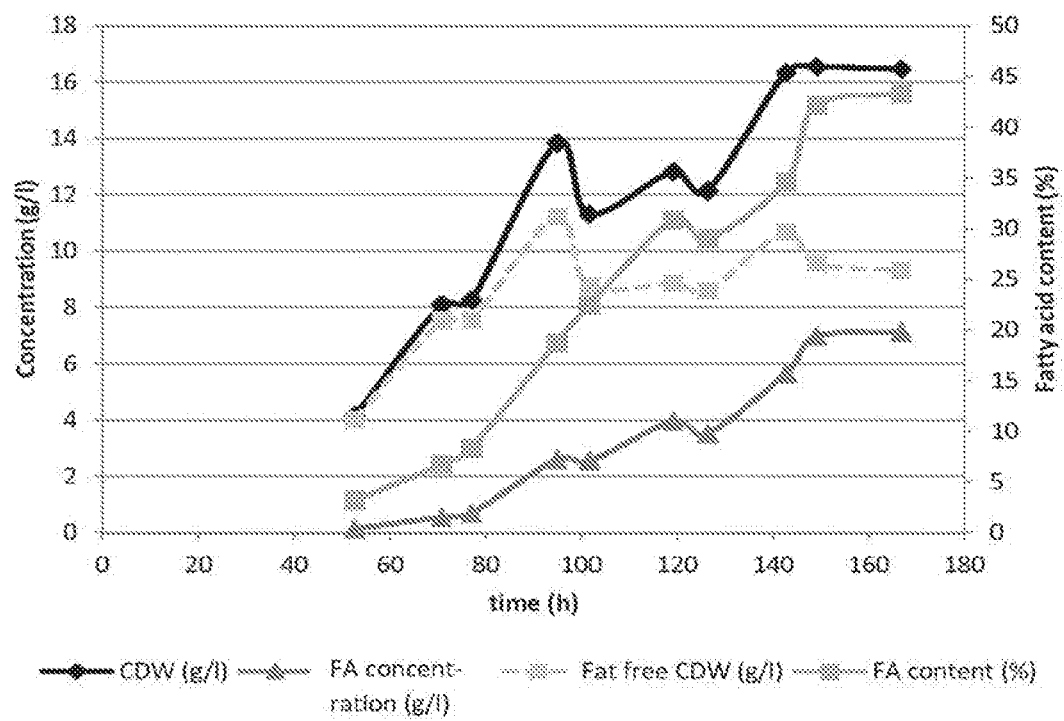
FIG. 14 presents performance (cell dry weigh (CDW) (g/l), fatty acid (FA) concentration (g/l), fat free cell dry weight (CDW) (g/l) and fatty acid (FA) content (%) in microbial biomass) of fed-batch fermentation with *Aspergillus. oryzae* on wheat straw cellulose and hemicellulose hydrolysates.

After inoculation it took about 30 h before the fungus started growing actively. During cultivation, the hemicellulose solution was added in small batches, and after 95 h of cultivation the feeds were changed to cellulosic hydrolysate. During the cultivation, in total 236 g of hemicellulose and 484 g cellulose hydrolysate was added. Part of the sugars added was left unutilized at the end of the fermentation. At 167 h, when the cultivation ended, there was 16 g/l of biomass, of which 43% lipids (FIG. 14). It could be concluded that producing microbial oil from wheat straw hemicellulose and cellulose sugars was successful.

Example 15

Producing Microbial Oil on Hemicellulosic Sugars

Preparation of Hydrolysate, Autohydrolysis Liquid D

A suspension was prepared by mixing 10.5 kg of milled wheat straw (92.7% dry matter content) and 54.1 kg of tap water in a 100 dm3 container. After storing at room temperature for 18 h, 64.2 kg of the suspension was weighed into a horizontal cylindrical 250 dm3 stirred autoclave reactor. The reactor was closed and heated within 75 min to 140° C., maintained at 140° C. for 5 h and cooled to room temperature within 30 min. The hydrothermally treated suspension was manually discharged from the reactor, and the first liquid fraction was separated from the first solid by filtration. The first solid fraction was washed twice with tap water and pressed using a hydro-press giving washed solid fraction. The washed solid fraction (20.9 kg) had 42.7% dry matter content. The first liquid fraction was combined with the wash-waters and concentrated in a falling film evaporator to 11.5% (w/w) dry matter content. The concentrated liquid, autohydrolysis liquid D, contained 49.3% total sugar from the total dry matter of the concentrated liquid as determined after dilute acid hydrolysis (4% w/w sulfuric acid, 121° C., 1 h) by high-performance liquid chromatography (HPLC). The relative proportions of anhydrous xylose, anhydrous arabinose, anhydrous glucose, and anhydrous galactose of the total sugar content were 57%, 19%, 13%, and 11%, respectively.

After this the autohydrolysis liquid D containing hemicellulosic sugars partly in oligomeric form was used in cultivation experiments as such without purification.

Single Cell Oil Production

The experiments were done using a lipid producing fungal strain A. oryzae. From the sporulating fungus grown on PDA-plates a spore suspension was made by adding 12 ml of sterile water and the spores were scraped off with inoculation loop to the liquid. 24 ml of the spore suspension was used for inoculation of 6 flasks. The medium composition is presented in table 5. The inoculated flasks were incubated at 30° C. 160 rpm shaking for 1 day, and then used for fermenter inoculation.

TABLE 5

Composition of inoculation medium, pH set to 5.5.

| | g/l |
|---|---|
| Hemicellulosic sugars | 40 |
| Yeast extract | 1 |
| (NH4)2SO4 | 1 |
| MgSO4 * 7H2O | 1 |
| K2HPO4 | 0.5 |
| KH2PO4 | 1 |
| CaCl2 * 2H2O | 0.2 |

Autohydrolysis liquid D (containing hemicellulosic sugars partly in oligomeric form) was used and it contained 4.2 g/l phenolic compounds based on analysis with Folin-Ciocalteu method (Waterhouse, 2002). The cultivation was done in Biostat B plus 5 l fermentor in 3 l volume, and during it the stirring was set to 400 rpm, pH was kept in 5.5 with 3 M NaOH, the aeration was 1 vvm and the temperature 30° C. The medium composition is presented in table 6.

TABLE 6

The composition of fermentation medium

| Medium components | Concentration (g/l) |
|---|---|
| Hemicellulosic sugars | 60 |
| Yeast extract | 1 |
| (NH4)2SO4 | 1 |
| MgCl * 6H2O | 1.0 |
| K2HPO4 | 0.5 |
| KH2PO4 | 1.0 |
| CaCl2 * 2H2O | 0.2 |

Results:

During cultivation, the hemicellulosic solution was added in small batches. In total 150 g of hemicellulose was added. Part of the sugars added was left unutilized at the end of the fermentation. At 142 h, when the cultivation ended, there was 14 g/l of biomass, of which 21% lipids. It could be concluded that producing microbial oil from wheat hemicellulosic sugars (partly in oligomeric form) was successful. Microbial oil production from hemicellulosic sugars was successful without the purification of the hydrolysate (other than evaporation used in the concentration of sugars). In the fermentation the concentration of phenolic compounds was 2.8 g/L.

Therefore, it could also be stated that fungal growth and lipid production was possible in spite of high inhibitor concentrations.

The invention claimed is:

1. A method for fractionation of a lignocellulosic material, the method comprising:
    a) Subjecting the lignocellulosic material to a delignification treatment in a presence of an alkaline delignification agent to produce a mixture containing a first solid phase and a first liquid phase containing dissolved lignin, wherein no acid pre-treatment is performed,
    b) Separating the first solid phase from the first liquid phase,
    c) After step b), introducing a cationic compound into the first liquid phase obtained from step b) without adjusting the pH of the first liquid phase prior to introducing the cationic compound, to produce a mixture containing a second solid phase and a second liquid phase, wherein the second liquid phase is separated from the second solid phase and the second liquid phase is recycled to step a),
    d) Subjecting the first solid phase to an enzymatic hydrolysis treatment in a presence of enzymes capable of hydrolysing the hemicellulose and cellulose fractions of the first solid phase to produce a mixture containing a third liquid phase formed as an enzymatic hydrolysate and a third solid phase; and
    e) Separating the third liquid phase from the third solid phase,
    wherein a concentration of delignification agent is from 0.1 to 4 wt %-, based on an amount of lignocellulosic material on dry matter basis,
    wherein cationic compound is selected from the group consisting of:
    cationic starch polysaccharides, cationic amylose, cationic amylopectin, cationic dextran, cationic lignin oligomers, cationic lignin polymers, cationic peat, and mixtures thereof, or
    wherein the cationic compound is an elemental cationic ion selected from the group consisting of: alkaline earth metals and bivalent and trivalent cations of iron (Fe) or aluminium (Al), and
    wherein the lignocellulosic material is subjected to a treatment wherein hemicellulose is at least partially removed from the lignocellulosic material as an aqueous hemicellulose hydrolysate, before the lignocellulosic material is subjected to step a).

2. The method according to claim 1, wherein the cationic polymers and oligomers have a cationic charge density of 0.5-5 meq/g.

3. The method according to claim 1, wherein the cationic ion is obtained from a compound selected from the group consisting of: AlCl3 aluminum chloride, Ba(C2H3O2)2 barium acetate, Ba(HCO3)2 barium bicarbonate, BaBr2 barium bromide, BaCl2 barium chloride, Ba(HCO2)2 barium formate, (Ba(OH)2 barium hydroxide), Ba(NO3)2 barium nitrate, Ca(C2H3O2)2 calcium acetate, Ca(HCO3)2 calcium bicarbonate, CaBr2 calcium bromide, CaCl2 calcium chloride, Ca(HCO2)2 calcium formate, (Ca(OH)2 calcium hydroxide), Ca(NO3)2 calcium nitrate, Mg(C2H3O2)2 magnesium acetate, Mg(HCO3)2 magnesium bicarbonate, MgBr2 magnesium bromide, MgCl2 magnesium chloride, Mg(HCO2)2 magnesium formate, (Mg(OH)2 magnesium hydroxide), Mg(NO3)2 magnesium nitrate, Fe(C2H3O2)2 iron acetate, FeCl3 ferric chloride, and corresponding hydrates.

4. A method for fractionation of a lignocellulosic material, the method comprising:
    a) Subjecting the lignocellulosic material to a delignification treatment in a presence of an alkaline delignification agent to produce a mixture containing a first solid phase and a first liquid phase containing dissolved lignin,
    b) Separating the first solid phase from the first liquid phase,
    c) After step b), without adjusting the pH of the first liquid phase prior to introducing the cationic compound, introducing a cationic compound into the first liquid phase obtained from step b) to produce a mixture containing a second solid phase and a second liquid phase, wherein the second liquid phase is separated from the second solid phase and the second liquid phase is recycled to step a),
    d) Subjecting the first solid phase to an enzymatic hydrolysis treatment in a presence of enzymes capable of hydrolysing the hemicellulose and cellulose fractions of the first solid phase to produce a mixture containing a third liquid phase formed as an enzymatic hydrolysate and a third solid phase; and e) Separating the third liquid phase from the third solid phase, wherein the amount of cationic compound is 0.001-0.25 g/g based on a dry matter content of the first liquid phase, wherein a concentration of delignification agent is from 0.1 to 4 wt %-, based on an amount of lignocellulosic material on dry matter basis, wherein cationic compound is selected from the group consisting of:

cationic starch polysaccharides, cationic amylose, cationic amylopectin, cationic dextran, cationic lignin oligomers, cationic lignin polymers, cationic peat, and mixtures thereof, or wherein the cationic compound is an elemental cationic ion selected from the group consisting of:

alkaline earth metals and bivalent and trivalent cations of iron (Fe) or aluminium (Al), and wherein the lignocellulosic material is subjected to a treatment wherein hemicellulose is at least partially removed from the lignocellulosic material as an aqueous hemicellulose hydrolysate, before the lignocellulosic material is subjected to step a).

5. The method according to claim 1, wherein the alkaline delignification agent is selected from a group consisting of:

sodium hydroxide, sodium carbonate, potassium hydroxide, potassium carbonate, calcium hydroxide, and calcium carbonate, lithium hydroxide, lithium carbonate, ammonium hydroxide, ammonia, sodium sulphide, and corresponding hydrates.

6. The method according to claim 1, wherein the alkaline delignification agent is added to the lignocellulosic material to obtain a suspension having a pH of above 7.

7. The method according to claim 1, wherein the hemicellulose is at least partly removed from the lignocellulosic material by hydrothermal treatment.

8. A method according to claim 1 for production of a microbial lipid, the method comprising:
(i) providing a cultivation medium having the liquid phase formed as an enzymatic hydrolysate of step e),
(ii) providing a fermentation broth by inoculating the cultivation medium with an oleaginous microbe,
(iii) incubating said medium inoculated with said oleaginous microbe to allow a lipid to accumulate, and
(iv) recovering the lipid from said oleaginous microbe.

9. The method for producing a microbial lipid, the method comprising:
a) Subjecting lignocellulosic material to a delignification treatment in a presence of an alkaline delignification agent to produce a mixture containing a first solid phase and a first liquid phase containing dissolved lignin,
b) Separating the first solid phase from the first liquid phase,
c) Introducing a cationic compound into the first liquid phase obtained from step b) without adjusting the pH of the first liquid phase prior to introducing the cationic compound, to produce a mixture containing a second solid phase and a second liquid phase,
d) Subjecting the first solid phase to an enzymatic hydrolysis treatment to hydrolyse hemicellulose and cellulose fractions of the first solid phase to produce a mixture containing a third liquid phase and a third solid phase containing lignin, and
e) Separating the third liquid phase from the third solid phase, by:
(i) providing a cultivation medium containing the third liquid phase formed as an enzymatic hydrolysate of step e),
(ii) providing a fermentation broth by inoculating the cultivation medium with an oleaginous microbe,
(iii) incubating said medium inoculated with said oleaginous microbe to allow the lipid to accumulate, and
(iv) recovering the lipid from said oleaginous microbe.

10. The method according to claim 1, wherein a concentration of delignification agent is 4 wt %-, based on an amount of lignocellulosic material on dry matter basis.

11. The method according to claim 1, wherein the alkaline delignification agent is added to the lignocellulosic material to obtain a suspension having a pH of above between 10 and 13.

12. The method according to claim 3, wherein the amount of cationic compound is 0.001-0.25 g/g based on a dry matter content of the first liquid phase.

13. The method according to claim 12, wherein the second liquid phase is separated from the second solid phase and the second liquid phase is recycled to step a).

14. The method according to claim 13, wherein a concentration of delignification agent is 0.1 wt %-, based on an amount of lignocellulosic material on dry matter basis.

15. The method according to claim 1, wherein the cationic compound is a cationic polymer or a cationic oligomer.

16. The method according to claim 1, wherein the enzymes comprise 1,4-β-glucanase, 1,4-β-glucosidase, or a hemicellulose-degrading enzyme.

\* \* \* \* \*